United States Patent [19]

Urry

[11] Patent Number: 5,250,516
[45] Date of Patent: Oct. 5, 1993

[54] BIOELASTOMERIC MATERIALS SUITABLE FOR THE PROTECTION OF BURN AREAS OR THE PROTECTION OF WOUND REPAIR SITES FROM THE OCCURRENCE OF ADHESIONS

[75] Inventor: Dan W. Urry, Birmingham, Ala.

[73] Assignee: UAB Research Foundation, Birmingham, Ala.

[21] Appl. No.: 184,407

[22] Filed: Apr. 21, 1988

Related U.S. Application Data

[63] Continuation-in-part of Ser. No. 900,895, Aug. 27, 1986, Pat. No. 4,783,523, and a continuation-in-part of Ser. No. 853,212, Apr. 17, 1986, abandoned.

[51] Int. Cl.$^5$ .............................................. A61K 37/00
[52] U.S. Cl. ....................................... 514/17; 514/18; 530/330
[58] Field of Search ...................... 530/330; 514/17, 18

[56] References Cited

U.S. PATENT DOCUMENTS 4,605,413 8/1986 Urry et al. .......................... 530/323

FOREIGN PATENT DOCUMENTS

WO87/06238 10/1987 PCT Int'l Appl. ................. 530/323

OTHER PUBLICATIONS

D. W. Urry et al., "A New Class of Elastomeric Biomaterials: Dynamic β-Spirals Comprised of Sequential Polypeptides," *Polym. Prepr.* (Am. Chem. Soc. Div. Polym. Chem.) (1983) 24(1):3-4.

D. W. Urry et al., "Temperature-correlated Force and Structure Development in Elastomeric Polypeptides: The Ile Analog of the Polypentapeptide of Elastin," *Biopolymers* (1986) 25:1939-1953.

D. W. Urry et al., "Compounding of Elastin Polypentapeptide to Collagen Analog: A Potential Elastomeric Prosthetic Material," *Biomat. Med. Dev. Art. Org.* (1981) 9(3):181-194.

D. W. Urry et al., "Prolyl Hydroxylation of the Polypentapeptide Model of Elastin Impairs Fiber Formation," *Biochem. and Biophys. Res. Comm.* (1979) 90(1):194-198.

*Primary Examiner*—Bernard Dentz
*Attorney, Agent, or Firm*—Cooley Godward Castro Huddleson & Tatum

[57] ABSTRACT

An elastomeric material, capable of reversibly contracting and relaxing by an inverse temperature transition, in a form suitable for use as a protective layer between a mammalian repair site and a second tissue site whereby adhesion involving said repair site and said second tissue site is substantially prevented.

19 Claims, 1 Drawing Sheet

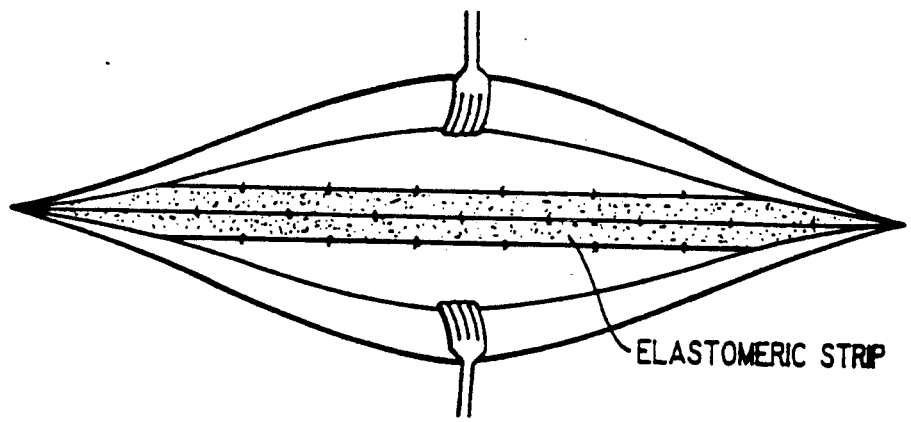
FIG. 1A TOPICAL VIEW OF BODY WALL INCISION
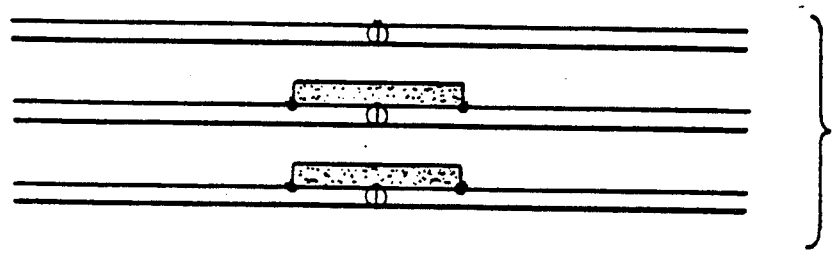
FIG. 1B CROSS-SECTION OF BODY WALL AT INCISION
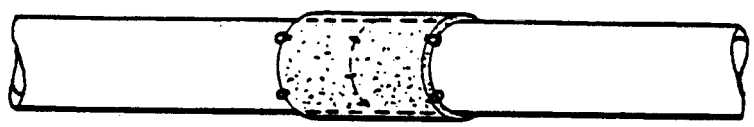
FIG. 1C RESECTIONED INTESTINE

BIOELASTOMERIC MATERIALS SUITABLE FOR THE PROTECTION OF BURN AREAS OR THE PROTECTION OF WOUND REPAIR SITES FROM THE OCCURRENCE OF ADHESIONS

BACKGROUND OF THE INVENTION

This application is a continuation-in-part application of U.S. Ser. No. 06/900,895 filed Aug. 27, 1986 now U.S. Pat. No. 4,783,523 and of U.S. Ser. No. 853,212 filed on Apr. 27, 1986 now abandoned.

FIELD OF THE INVENTION

This invention relates to bioelastic materials which are suitable for the protection of burn areas or the protection of wound repair sites from the development of debilitating adhesions.

DESCRIPTION OF THE BACKGROUND

Adhesions accompanying the healing of wounds, whether due to surgery or other trauma, give rise to many disadvantageous effects. For example, peritoneal cavity adhesions lead to intestinal obstruction and necessitate recurring operations. Furthermore, unwanted adhesions themselves pose problems during recurrent operations. For example, tendon adhesions often compromise tendon surgery and repair. Clearly, it would be extremely advantageous to find a suitable material that could function as an insulator material isolating wound repair sites from adhesions whether between layers of abdominal and thoracic walls, between repair sites within the abdomen or thorax, within the hand, wrist, foot, ankle, and other joints or between the skin and body stroma. However, such a material would have to satisfy many prerequisites. For example, it would be necessary that such a material would match the compliance of the soft tissue site of application. The material would also need to be biodegradable and be obtainable in different forms, such as elastomeric sheets, foams or powders, that would provide sufficient ease of handling for each particular application. Of course, such a material would also have to be readily sterilizable as well as being biocompatible and eliciting insignificant immunogenic and antigenic responses in the host.

The same properties described above would also be advantageous in a material for the protection of burn areas and to facilitate repair of the damaged tissue.

At present, a material which fully meets all of the above requirements is unknown.

SUMMARY OF THE INVENTION

Accordingly, it is an object of the present invention to provide an elastomeric material which is compatible with and similar to the soft tissue at wound sites, and which is also biodegradable.

It is also an object of the present invention to provide an elastomeric material which may be prepared in different forms, such as sheets, gels, foams or powders, that provide sufficient ease of handling for various applications.

Furthermore, it is also an object of the present invention to provide an elastomeric material which is readily sterilizable and which elicits insignificant immunogenic and antigenic responses.

Furthermore, the present invention also provides a process for isolating wound repair sites to effect a more salutary wound healing process.

According to the present invention, the foregoing and other objects are obtained by providing a biomaterial containing an effective amount of an elastomeric polypeptide and water, and wherein said elastomeric polypeptide has an adjustable elastic modulus.

In particular, the present invention provides an elastomeric material, capable of reversibly contracting and relaxing by an inverse temperature transition, in a form suitable for use as a protective layer between a mammalian repair site and a second tissue site, whereby the elastomeric material is capable of substantially preventing adhesion between the repair site and the second tissue site.

BRIEF DESCRIPTION OF THE DRAWINGS

FIG. 1(a) is a topical view of a body wall incision covered with an elastomeric strip of the present invention.

FIG. 1(b) is a cross-section of a body wall incision with the sutured sites of each layer separated one from the other by elastomeric strips.

FIG. 1(c) is an illustration of a resectioned intestine, the sutured site of which is protected by a sleeve of the present elastomeric material.

DETAILED DESCRIPTION OF THE PREFERRED EMBODIMENTS

The present invention uses elastomeric polypentapeptides such as $(VPGVG)_n$ as a matrix which may then be modified in a variety of ways to obtain particular properties. For example, the polyhexapeptide $(VAPGVG)_n$ may be added either in parallel or in sequence to increase strength, elastic modulus and ease of handling. Furthermore, for specific applications, cell attachment sequences for appropriate tissue cells, may be added covalently and sequentially to provide for the desired cell adhesion as in a tendon sheath or in a fascia or in burn covers.

The elastomeric polypeptides of the present invention have the ability to control adhesions at wound repair sites. Under physiological conditions, the present biomaterials contain an effective amount of an elastomeric polypeptide and water. Moreover, the present polypeptides are biodegradable, biocompatible and are readily sterilizable. Furthermore, the present biomaterials may be formed in cross-linked sheets or strips varying from a gelatinous to a teflon-like consistency and it is even possible to prepare these materials in a deformable foam-like state with or without cross-linking. Also when efficacious the sequential polypeptide could be applied as a powder which on absorbing water is a sticky viscoelastic gel-like material.

Of particular interest are the polypeptides containing repeating peptide sequences that occur naturally within the elastic fiber of biological connective tissue. The primary sequential polypeptides are $(VPGVG)_n$ and $(VAPGVG)_n$. The polypentapeptide is biocompatible and biodegradable as a soft tissue implant and, also as a natural component of connective tissue. The same is true for the polyhexapeptide. The biomaterial is sterilizable as it withstands autoclaving conditions and is cross-linkable to form elastomeric matrices by γ-irradiation at 10-30 Mrad. By varying the proportions of polypentapeptide and polyhexapeptide in the bioelastomer as well as the Mrad dosage, the elastic modulus may be varied and the material consistency can be changed from gelatinous to teflon-like. In addition to cross-linking by γ-irradiation, other means of cross-linking may be used so long as they are biocompatable.

I. The Elastomeric Materials

Elastin is comprised of a single protein. The sequence of elastin can be described as a serial alignment of alanine-rich, lysine-containing cross-linking sequences alternating with glycine-rich hydrophobic sequences. With the entire bovine sequence known, the most striking hydrophobic sequences, both from the standpoint of length and of composition, are one that contains a polypentapeptide (PPP) and one that contains a polyhexapeptide (PHP). Elastin also contains a repeating polytetrapeptide (PTP). As a result of work conducted by the present inventors, the polypentapeptide of elastin when cross-linked has been found to be elastomeric and the polyhexapeptide thereof has been found to be non-elastomeric and appears to provide a means for aligning and interlocking the chains during elastogenesis. From the present work, it has now also been found that the elastin polypentapeptide and polytetrapeptide are both conformation-based elastomers that develop entropic elasticity and strength on undergoing an inverse temperature transition to form a regular β-turn containing dynamic structure.

A typical biological elastic fiber is comprised of a large elastin core covered with a fine surface layer of microfibrillar protein. Elastin is formed upon cross-linking of the lysine residues of tropoelastin. The repeating elastin pentapeptide has the formula $(VPGVG)_n$, while the repeating hexapeptide has the formula $(VAPGVG)_n$, where n varies depending upon the species. The repeating polytetrapeptide unit has the formula $(VPGG)_n$. These sequences, of course, utilize the standard one-letter abbreviation for the constituent amino acids.

It has been found that these polypeptides are soluble in water below 25° C., but on raising the temperature they associate in the polypentapeptide (PPP) and polytetrapeptide (PTP) cases, reversibly to form a viscoelastic phase, and in the polyhexapeptide (PHP) case, irreversibly to form a precipitate. On cross-linking, the former (PPP) and (PTP) have been found to be elastomers.

In part, the present material contains PPP, which exhibits aggregation and forms a water-containing viscoelastic phase, which upon cross-linking by γ-irradiation forms an elastomer. By contrast, PHP forms a granular precipitate, which is not elastomeric. In fact, it has been found that for potential elastomers, such aggregation is reversible, whereas for non-elastomeric samples, such as PHP, temperature-driven aggregation is irreversible in water and redissolution usually requires the addition of trifluoroethanol to the aggregate.

For purposes of clarification, it is noted that the reversible temperature elicited aggregation, which gives rise upon standing to a dense viscoelastic phase, is called coacervation. The viscoelastic phase is called the coacervate, and the solution above the coacervate is referred to as the equilibrium solution.

Most importantly, however, cross-linked PPP, PTP and analogs thereof at fixed length exhibit elastomeric force development at different temperatures spanning a range of up to about 75° C. depending upon several controllable variables. Moreover, these cross-linked elastomers develop near maximum elastomeric force over a relatively narrow temperature range. Thus, by synthesizing bioelastomeric materials having varying molar amounts of the constituent pentamers and tetramers together with such units modified by hexameric repeating units, and by choosing a particular solvent to support the initial viscoelastic phase, it is possible to rigorously control the temperature at which the obtained bioelastomer develops elastomeric force.

In general, the process of raising the temperature to form the above elastomeric state is an inverse temperature transition resulting in the development of a regular non-random structure, unlike typical rubbers, which utilizes, as a characteristic component, hydrophobic intramolecular interactions. The regular structure is proposed to be a β-spiral, a loose water-containing helical structure with β-turns as spacers between turns of the helix which provides hydrophobic contacts between helical turns and has suspended peptide segments. These peptide segments are free to undergo large amplitude, low frequency rocking motions called librations. Consequently, a new mechanism of elasticity has now been developed called the librational entropy mechanism of elasticity.

The elastomeric force of these various bioelastomers develops as the regular structure thereof develops. Further, a loss of regular structure by high temperature denaturation, results in loss of elastomeric force. Interestingly, this situation is just the reverse of that for the random-chain-network theory of elasticity, in which the more nearly random the polypentapeptide, the less the elastomeric force, and the more developed the β-turn containing structure, the greater the elastomeric force.

In the broadest sense, a new entropy-based mechanism of elasticity is presented for use herein. The mechanism therefor appears to be derived from a new class of polypeptide conformations called β-spirals wherein β-turns recur with regularity in a loose water-containing helix. The β-spiral is the result of intramolecular interturn hydrophobic interactions which form on raising the temperature in water. In the β-spiral of the elastomeric polypentapeptide of elastin, $(Val^1\text{-}Pro^2\text{-}Gly^3\text{-}Val^4\text{-}Gly^5)_n$, the type II $Pro^2\text{-}Gly^3$ β-turns function as spacers, with hydrophobic contacts, between the turns of the helix, which results in the segments of $Val^4\text{-}Gly^5\text{-}Val^1$ being suspended. Being essentially surrounded by water, the peptide moieties of the suspended segments are free to undergo large rocking motions referred to as librations which become damped on stretching. The decrease in amplitude of librations and increase in their frequency on stretching constitutes a decrease in entropy and it appears that the decrease in free energy due to the increase in entropy on returning to the relaxed state is the driving force for elastomeric retraction.

Upon raising the temperature of the polypeptide-solvent system, such as PPP-water, for example, the hydrophobic side chains such as those of Pro and Val when dispersed in water are surrounded by water having a clathrate-like structure, that is, by water that is more ordered than normal bulk water. Upon raising the temperature, an amount of this more ordered clathrate-like water surrounding the hydrophobic groups becomes less ordered bulk water as the hydrophobic chains associate to form a more ordered polypeptide. It appears that it is the optimization of intramolecular hydrophobic contact that assists the polypeptide in wrapping up into a loose helix. Adherence to the Second Law of Thermodynamics appears to be maintained by the requirement that the decrease in entropy of the polypeptide portion of the system be less than the increase in entropy of the water in system. Since $\Delta G=0$ at the temperature midpoint ($T_{mp}$) of a structural transition between a pair of states, then $T_{mp}=\Delta H/\Delta S$. If the entropy change, $\Delta S$, derives from the hydrophobicity of the repeating unit, as it would in the clathrate-like water mechanism, than an increase in the hydrophobicity of the repeating unit can be used to explain the decrease in $T_{mp}$, the midpoint of the inverse temperature transition. In fact, a decrease in the hydrophobicity of the repeating unit results in an increased $T_{mp}$. Conversely, an increase in the hydrophobicity of the repeating units results in a decrease in $T_{mp}$.

The above principle is demonstrated by substituting the more hydrophobic isoleucine (Ile) for valine (Val) in the elastin polypentapeptide, $(Ile^1-Pro^2-Gly^3-Val^4-Gly^5)_n$, i.e., $Ile^1$-PPP, to produce a substituted polypentapeptide which has properties similar to PPP, except that the described transition occurs at a lower temperature.

For purposes of clarity, it is noted that for the above numbered sequence and all sequences hereafter, the superscript numbering system is a sequence numbering based upon the dominant secondary structural feature of these repeating sequences which is the type II $Pro^2$-$Gly^3$ $\beta$-turn, a ten atom hydrogen bonded ring involving the C=O of residue 1 and the NH of residue 4.

The present elastomeric materials also extend to the polytetrapeptide of elastin. It is recalled that this repeating unit has the formula $(Val^1-Pro^2-Gly^3-Gly^4)_n$, which also forms a $\beta$-spiral similar to PPP. However, the temperature of aggregation for PTP occurs at a higher temperature than for PPP. In essence, for both the polypentapeptide and polytetrapeptide repeating units of elastin, it has been found that the temperature of the transition for the development of elastomeric force is inversely proportional to the hydrophobicity of the repeating unit. Hence, two important principles have been elucidated. First, elastomeric force development at fixed lengths or the shortening at fixed force occurs due to an inverse temperature transition resulting in increased polypeptide order by raising the temperature. Secondly, the temperature of this transition for the development of elastomeric force for contraction is inversely proportional to the hydrophobicity of the repeating unit in the bioelastomer.

Analogs of both the elastin polypentapeptide PPP and the polytetrapeptide (PTP) and combinations thereof are contemplated for use in the present invention. For example, it has been found that the temperature of transition for $Ile^1$-PPP shifts to a lower temperature by an amount calculable from the increase in hydrophobicity relative to PPP using hydrophobicity scales. Thus, by carefully choosing a new analog with a different repeating unit hydrophobicity, the transition temperature for the development of elastomeric force can be predictably shifted to a different temperature. In fact, it has been shown that by judiciously selecting various repeating units and combinations thereof, along with various solvent mixtures it is now possible to select a transition temperature from within a range of up to about 75° C., from about −25° C. to about +50° C.

Additionally, the elastin polyhexapeptide (PHP) may also be incorporated in various amounts in the elastomeric materials of the present invention as will be discussed below.

The most striking repeating sequence of bovine and porcine elastin is the polypentapeptide $(Val^1-Pro^2-Gly^3-Val^4-Gly^5)_n$, wherein, for example, n is 11 for cows and pigs. The polypentapeptide is soluble in water at all proportions below 25° C. On raising the temperature above 25° C., aggregation occurs and the aggregate settles to form a dense viscoelastic phase, called a coacervate, that at 40° C. is about 38% peptide and 62% water by weight. The process of PPP coacervation, as noted, is entirely reversible. Moreover, on crosslinking, the PPP coacervate is found to be elastomeric. The coacervate concentration of PPP as well as the elastomeric $\gamma$-irradiation cross-linked ppp coacervate undergo an inverse temperature transition, which commences at 25° C. and which reaches completion near 37° C. Over the same temperature range, the elastomeric force of the cross-linked PPP coacervate at fixed length increases dramatically or the length at fixed force shortens dramatically on raising the temperature from near zero at 20° C. to full force or full contraction near 40° C. Above 40° C., the elastomeric force or length divided by the temperature (°K) becomes quite constant.

This indicates that the cross-linked PPP is a dominantly entropic elastomer. That is, the entropic component of the elastomeric force depends upon the decrease in numbers of low energy states accessible to the polymer on extension, whereas a large internal energy component of elastomeric force would result from stressing of bonds which would increase the probability of rupture of the elastomer.

Thus, in part, the materials of the present invention are of a nature such that it is possible to change the temperature of transition by modifying the PPP. In particular, it has been found that by increasing the hydrophobicity of the PPP repeating unit, the viscoelastic phase transition occurs at lower temperatures, while by decreasing the hydrophobicity of the repeating units, this transition occurs at higher temperatures. Of course, when modifying the hydrophobicity, it is necessary to do so in a way such that elasticity is retained.

For example, modifications of the repeating pentamers have been made which destroy the molecular structure required for elasticity, such as the $Ala^1$ and $Ala^5$ analogs. The $Ala^1$ and $Ala^5$ analogs, the former decreasing and the latter increasing pentamer hydrophobicity, result in the formation of granular precipitates on raising the temperature of aqueous solutions rather than forming viscoelastic coacervates and $\gamma$-irradiation cross-linking of the $Ala^5$-PPP precipitate results in a hard material that simply breaks upon stretching. In accordance with the present discovery, it is believed that these analogs fail to produce elastomeric polymers for different but consistent reasons. First, the $Ala^1$ analog does not appear to allow for important $Val^1$ $\gamma CH_3$... $Pro^2 \delta CH_2$ intramolecular hydrophobic contacts required to form a viscoelastic coacervate. The $Ala^5$ analog appears to interfere with librational motions in the $Val^4-Gly^5-Val^1$ suspended segment of the proposed PPP molecular structure. As noted, the librations are central to the proposed librational entropy mechanism of elasticity.

By contrast, the hydrophobicity of the repeating pentamer can be easily increased by introducing a-$CH_2$-moiety, for example, in residue 1 while maintaining $\beta$-branching, that is, to utilize the $Ile^1$ analog of PPP, i.e., $(Ile^1-Pro^2-Gly^3-Val^4-Gly^5)_n$. With a greater than 50,000 molecular weight, $Ile^1$-PPP reversibly forms a viscoelastic coacervate with the onset of coacervation being at 8° C. rather than 24° C. as for unsubstituted PPP. It appears from circular dichroism data that $Ile^1$-

PPP and PPP have identical conformations both before and after the transitions and that the transition to increased intramolecular order on increasing the temperature is also shifted by 15° C. or more to lower temperatures. Further, the dramatic increase in elastomeric force on raising the temperature of the γ-irradiation cross-linked coacervate is similarly shifted to a lower temperature for the Ile$^1$-PPP analog. Thus, with this analog, a coupling of temperature dependent elastomeric force development and molecular structure is demonstrated. This, of course, means that it is now possible to rationally design polypeptide elastomers that undergo transitions at different temperatures and that would function as entropic elastomers in different temperature ranges.

As noted above, by increasing the hydrophobicity of PPP, such as by substituting Ile$^1$ for Val$^1$ in the pentameric sequence of —(VPGVG)$_n$ to form —(IPGVG)$_n$, it is now possible to accomplish at least two distinct objectives.

First, it is now possible to prepare, for example, the "homopolymeric" polypentapeptide of —(IPGVG)—$_n$, i.e., Ile$^1$-PPP, which, as noted dissolves in water at 4° C., and upon raising the temperature to 8° C., exhibits aggregation. After cross-linking the coacervate by γ-irradiation, it is observed for a fixed length that essentially full elastomeric force is exhibited at about 25° C. for the cross-linked Ile$^1$-PPP as opposed to the 40° C. temperature required for the unsubstituted PPP. Thus, the temperature of the ordering transition for Ile$^1$-PPP occurs at a temperature approximately 15° C. lower than for PPP.

Secondly, it is now also possible to prepare mixed "copolymers", for example, of the polypentapeptides —X$^1$—(IPGVG)$_n$—Y$^1$— and —X$^2$—(VPGVG—)-$_n$—Y$^2$— which exhibit variable and controllable transition temperatures which are in between the separate transition temperatures of PPP and Ile$^1$-PPP. Further, a great degree of control is possible inasmuch as the transition temperature obtained is proportional to the molar ratios of the respective pentapeptides incorporated therein.

Although Ile$^1$-PPP is an excellent example of an increased hydrophobicity PPP analog, any PPP analog, which reduces the hydrophobicity of the repeating pentameric unit, while retaining the elasticity of the polypeptide, and without interfering with either the formation of the viscoelastic coacervate or the librational motion is characteristic of the materials to be utilized in the prevention of adhesion.

For example, in addition to repeating unit sequences of 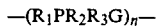$_n$, using Ile$^1$, it is also possible to effect a variety of other substitutions. In general, a pentapeptide repeating unit of the formula:

—(R$_1$PR$_2$R$_3$G)$_n$— is also capable of being used in the materials of the present invention, wherein R$_1$ is selected from the group consisting of Phe, Leu, Ile, and Val; R$_2$ is selected from the group consisting of Ala and Gly; R$_3$ is selected from the group consisting of Phe, Leu, Ile, and Val; and n is an integer from 1 to 5,000; and P is L-proline and G is glycine.

Notably, the above substitutions modify the hydrophobicity of the repeating unit so as to attenuate the transition temperature for near maximum elastomeric force development, of course, without destroying the elasticity of the bioelastomer.

In the above formula, it is noted that the amino acid Leu is, of course, leucine and Phe is phenylalanine. The three-lettered abbreviations used in the present specification are the standard abbreviations for amino acids. R$_1$, R$_2$ and R$_3$ correspond to positions 1, 3 and 4 in the numbered sequence as described herein.

As noted previously, the materials of the present invention include not only PPP analogs, such as Ile$^1$-PPP, Phe$^1$-PPP or Ala$^3$-PPP but all PPP analogs, and bioelastomers containing the same, which have transition temperatures, and, hence, temperatures of near maximum elastomeric force development, which are appropriate to the site of application. Given, the present disclosure, one skilled in the art could clearly ascertain additional PPP analogs, and bioelastomers incorporating the same which meet the above criteria.

As noted above, the increased hydrophobicity analog, such as Ile$^1$-PPP may be synthesized as a "homopolymer", or a "copolymer" of —X$^2$—(VPGVG—)-$_n$—Y$^2$— and —X$^1$—(IPGVG—)$_n$—Y$^1$— may be synthesized with the molar ratio of the constituent pentamers being dependent upon the desired temperature for elastomeric force development. However, in general, in such "copolymers", the —X$^1$—(IPGVG—)$_n$—Y$^1$— pentameric component is present in about 1-99% of the total pentameric molar content, while the —X$^2$—(VPGVG—)$_n$—Y$^2$— pentameric component is present in about 99-1% of the total pentameric molar content. More preferably, the —X$^1$—(IPGVG)$_n$—Y$^1$— component is present in about 5-95% of the total pentameric molar content, while the —X$^2$—(VPGVG—)-$_n$—Y$^2$— component is present in about 95-5% of the total pentameric molar content. However, any combination of relative molar amounts can be used as dictated by the desired transition temperature.

Thus, in accordance with one aspect of the present invention, bioelastomers can be prepared which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises a polypentapeptide unit of the formula:

wherein

I is a peptide-forming residue of L-isoleucine;
P is a peptide-forming residue of L-proline;
G is a peptide-forming residue of glycine;
V is a peptide-forming residue of L-valine; and
wherein X is PGVG, GVG, VG, G or a covalent bond;
Y is IPGV, IPG, IP or I or a covalent bond; and n in both formulas is an integer from 1 to 5,000; or n is 0, with the proviso that X$^1$ and Y$^1$ together constitute a repeating pentapeptide unit, in an amount sufficient to adjust the development of elastomeric force of the bioelastomer to a predetermined temperature.

However, the present invention also relates, as noted above, to bioelastomers which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises A) a polypentapeptide unit of the formula:

and B) a polypentapeptide unit of the formula:

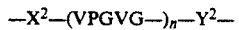

wherein for the above formulas,
I is a peptide-forming residue of L-isoleucine;
P is a peptide-forming residue of L-proline;
G is a peptide-forming residue of glycine;
V is a peptide-forming residue of L-valine; and
wherein $X^1$ and $X^2$ are each PGVG, GVG, VG, G or a covalent bond; $Y^1$ is IPGV, IPG, IP or I or a covalent bond; $Y^2$ is VPGV, VPG, VP, V or a covalent bond; and n in both formulas an integer from 1 to 5,000; or n in both formulas is 0, with the proviso that $X^1$ and $Y^1$ together, and $X^2$ and $Y^2$ together constitute a repeating pentapeptide unit, in relative amounts sufficient to adjust the development of elastomeric force of the bioelastomer to a predetermined temperature.

It should be noted that bioelastomeric polypeptide chains containing either one or both of the above pentapeptide repeating units can be synthesized using any of the pentapeptide "monomers" that are permutations of the basic sequence. However, if the polymer is not synthesized using the pentapeptide "monomers", but rather is synthesized by sequential adding of amino acids to a growing peptide, such as in the case of an automatic peptide synthesizer, the designation of the repeating unit is somewhat arbitrary. For example, the peptide HV(PGVGVPGVGVPGVGVPGVGV)P-OH can be considered to consist of any of the following repeating units and end groups: H-(VPGVG)$_4$-VP-OH, H-V-(PGVGV)$_4$-P-OH, H-VP-(GVGVP)$_4$-OH, H-VPG-(VGVPG)$_3$-VGVP-OH, or H-VPGV-(GVPGV)$_3$-GVP-OH, for example.

Furthermore, it is entirely possible and within the ambit of the present invention that mixed repeating units such as those of the formula $\pm$VPGVGIPGV-G$\pm_n$ can be incorporated into the bioelastomers of the present invention.

Synthesis of the elasticity promoting and modifying segments, which are incorporated into the final elastomeric polypeptide, is straightforward and easily accomplished by a peptide chemist or by standard methods of microbial fermentation using recombinant DNA. The resulting intermediate peptides generally have the structure, $B^1$—(repeating unit)$_n$—$B^2$, where $B^1$ and $B^2$ represent any chemically compatible end group on the amino and carboxyl ends of the molecule, respectively, and n is an integer of from 2 to about 5,000. Of course, when $B^1$ is —H and $B^2$ is —OH, and n is 1, the compound is either the pentapeptide H-VPGVG-OH or H-IPGVG-OH. When n is greater than 1, the compound intermediate is a polypentapeptide. The same will hold true when utilizing tetrameric repeating units in the present bioelastomers.

It should be noted that the term "hydrophobic amino acid" refers to amino acids which have appreciably hydrophobic R groups as measured on a hydrophobicity scale generated by measuring the relative solubilities of the amino acids in organic solvents or by their relative effects on surface tension. In this respect, see *Arch. Biochem. Biophy*, Bull and Breese, Vol. 161, 665–670 (1974). By this method, all amino acids which are more hydrophobic than glycine may be used. More specifically, preferable hydrophobic amino acids are Ala, Val, Leu, Ile and Pro.

It should also be noted that it is entirely possible that one or more amino acid residues or segments of amino acid residues not present in the normal pentapeptide or tetrapeptide sequence may be interspersed within a polypentapeptide or polytetrapeptide portion of an elastomeric polypeptide chain.

The bioelastomers of the present invention, regardless of the particular functional repeating unit incorporated therein, may have these repeating units incorporated either in the form of block or random copolymers as long as the desired shift in temperature of elastomeric force development of the bioelastomer is obtained. As noted above, by considering the transition temperatures and temperatures of elastomeric force development for two PPP or PTP analogs, or even for a PPP analog and a PTP analog, it is possible to attain a desired biodegradability and biocompatability.

Additionally, it is also noted that the elastomeric units used in conjunction with all aspects of the present invention, i.e., whether the repeating unit is PPP, PTP or analogs thereof, may also comprise those described in U.S. Pat. Nos. 4,187,852; 4,474,851; 4,500,700, 4,589,882, 4,605,413 and 4,693,718 and U.S. patent applications Ser. No. 853,212, 900,895 and 062,557, all of which patents and patent applications are incorporated herein in their entirety.

The aspect of the present invention with respect to PPP and analogs thereof will now be illustrated by Examples, which are provided only for the purpose of illustration and are not intended to limit the present invention.

EXAMPLES

Peptide Synthesis

The synthesis of Ile$^1$-PPP was carried out by the classical solution methods as shown in Scheme I.

In the following Examples, the following abbreviations will be used: Boc, tertbutyloxycarbonyl; Bzl, benzyl; DMF, dimethylformamide; DMSO, dimethylsulfoxide; EDCI, 1-(3-dimethylaminopropyl)-3-ethylcarbodiimide; HOBt, 1-hydroxybenzotriazole; IBCF, isobutyl-chloroformate; NMM, N-methylmorpholine; ONp, p-nitrophenylester; TFA, trifluoroacetic acid; PPP, (VPGVG)$_n$; Ile$^1$-PPP, (IPGVG)$_n$; V, valine; I, isoleucine; P, proline; G, glycine.

Scheme I
Synthesis of H—(Gly—Val—Gly—Ile—Pro)$_n$—OH

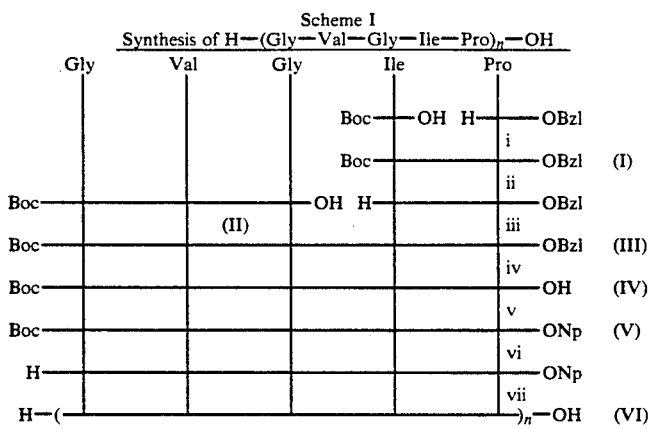

i) IBCF/HOBt;
ii) HCl/Dioxane;
iii) EDCI/HOBT;
iv) H2—Pd/C;
v) Bis(p-nitrophenyl)carbonate;
vi) TFA;
vii) DMSO—NMM The sequence of the starting pentamer for polymerization is preferably Gly-Val-Gly-Ile-Pro rather than Ile-Pro-Gly-Val-Gly, because the permutation with Pro as the C-terminal amino acid produces high molecular weight polymers in better yields. The approach to the synthesis entailed coupling the tripeptide Boc-GVG-OH (II) with H-IP-OBzl, each in turn being synthesized by the mixed anhydride methodology of J. R. Vaughan et al, *J. Am. Chem. Soc.,* 89, 5012 (1967). The possible formation of the urethane as a by-product during the reaction of Boc-Ile-OH with H-Pro-OBzl by the mixed anhydride method was avoided by carrying out the reaction in the presence of HOBt. The dipeptide was also prepared using EDCI for confirmation of the product. The pentapeptide benzylester (III) was hydrogenated to the free acid (IV) which was further converted to the p-nitrophenylester (V) on reacting with bis(p-nitrophenyl)carbonate. On removing the Boc-group, a one molar solution of the active ester in DMSO was polymerized in the presence of 1.6 equiv. of NMM. The polypeptide was dialyzed against water using a 50,000 dalton cut-off dialysis tubing and lyophilized. The purity of the intermediate and final products was checked by carbon-13 nuclear magnetic resonance, elemental analyses and thin layer chromatography (TLC).

Elemental analyses were carried out by Mic Anal, Tuscon, Ariz.. All amino acids are of L-configuration except for glycine. Boc-amino acids were purchased from Bachem, Inc., Torrance, Calif. HOBt was obtained from Aldrich Chemical Co., Milwaukee, Wis. TLC was performed on silica gel plates purchased from Whatman, Inc., Clifton, N.J. in the following solvent systems: $R_f^1$, CHCl$_3$ (C):CH$_3$OH(M):CH$_3$COOH(A), 95:5:3 $R_f^2$, CMA (85:15:3); $R_f^3$, CMA (75:25:3); $R_f^4$, CM (5:1). Melting points were determined with a Thomas Hoover melting point apparatus and are uncorrected.

Boc-Ile-Pro-OBzl (mixed anhydride method) (I): Boc-Ile-OH (12.01 g. 0.05 mole) in DMF (50 ml) was cooled to 0° C. and NMM (5.49 ml) was added. After cooling the solution to −15° C. isobutylchloroformate (6.48 ml) was added slowly while maintaining the temperature at −15° C. and stirred for 10 minutes at which time HOBt (7.65 g) was added and stirring was continued for additional 10 minutes. A pre-cooled solution of HCL-H-Pro-OBzl (12.09 g. 0.05 mole) in DMF (50 ml) and NMM (5.49 ml) was added to the above solution and the completeness of the reaction was followed by TLC. The reaction mixture was poured into a cold saturated NaHCO$_3$ solution and stirred for one hour. The peptide was extracted into CHCl$_3$ and washed with acid and base (0.5N NaOH to remove HOBt), and on evaporting the solvent the product was obtained as an oil in 92% yield. $R_f^1$, 0.65. Anal. Calcd. for C$_{23}$H$_{34}$N$_2$O$_5$: C 66.00, H 9.19, N 6.69%. Found: C 65.58, H 8.28, N 7.13%.

Boc-Ile-Pro-OBzl (using EDCI): Boc-Ile-OH (7.20 g, 0.03 mole) and HOBt (5.05 g, 0.033 mole) in DMF (30 ml) was cooled to −15° C. and EDCI (6.32 g, 0.033 mole) was added. After stirring for 20 minutes, a pre-cooled solution of HCl-H-Pro-OBzl (7.25 g, 0103 mole) in DMF (30 ml) and NMM (3.3 ml) was added and stirred overnight at room temperature. After evaporating DMF, the residue was taken into CHCl$_3$ and extracted with 20% citric acid and 0.5N NaOH. The solvent was removed and the product was obtained as an oil in almost quantitative yield which was identical to the product obtained by the mixed anhydride method.

Boc-Gly-Val-Gly-Ile-Pro-OBzl (III): Boc-GVG-OH (II) (20) (5.6 g, 0.017 mole) was coupled with H-IlePro-OBzl (6.7 g, 0.019 mole) (obtained by deblocking I with HCl/Dioxane) in the presence of EDCI (3.65 g, 0.019 mole) and HOBt (2.9 g, 0.019 mole) and the product was worked up as described above to obtain 8.8 g of III (yield: 82.4%), m.p. 107°-108° C. (decomp.) $R_f^1$, 0.44; $R_f^2$, 0.75. Anal. calcd. for C$_{32}$H$_{49}$N$_5$O$_{10}$: C 60.83, H 7.81, N 11.08%. Found: C 61.12, H 8.06, N 11.06%

Boc-Gly-Val-Gly-Ile-Pro-OH (IV): III (7.8 g, 0.0123 mole) was taken in acetic acid (80 ml) and hydrogenated in the presence of 10% Pd-C (1 g) at 40 psi. After filtering the catalyst with the aid of celite, the solvent was removed under reduced pressure, triturated with ether, filtered, washed with ether then pet. ether and dried to obtain 6.5 g of the product (yield: 97.3%), m.p. shrinks at 127° C. and decomp. at 3 145° C. $R_f^3$, 0.24; $R_f^4$, 0.11. Anal. Calcd. for C$_{25}$H$_{43}$N$_5$O$_{10}$.1/2H$_2$O: C 54.52, H 8.05, N 12.7%. Found: C 54.32, H 8.02, N 12.59%.

Boc-Gly-Val-Gly-Ile-Pro-ONp (V): IV (5.41 g, 0.01 mole) in pyridine (40 ml) was reacted with bis(pnitrophenyl)carbonate (4.56 g, 0.015 mole) following the completeness of the reaction by T@C. Pyridine was removed; the residue was taken into $CHCl_3$ and extracted with acid and base. The p-nitrophenyl ester obtained was chromatographed over a silica gel (200–400 mesh) column. After initial washing with $CHCl_3$, 4.8 g of V was obtained when eluted with 35% acetone in $CHCl_3$ (yield: 71.4%), m.p. 97°–100° C. $R_f^A$, 0.72; $R_f^A$, 0.75; Anal. Calcd. for $C_{31}H_{46}N_6O_{12}.2H_2O$: C 53:28, H 7.21, N 12.02%. Found: C 53.76, H 6.83, N 12.01%.

H-(Gly-Val-Gly-Ile-Pro)n-OH(VI): The Boc-group was removed from V (3.8 g, 0.0057 mole) by reacting with TFA (35 ml) for 45 min. TFA was removed under reduced pressure, triturated with ether, filtered, washed with ether, pet. ether and dried. The TFA salt (3.3 g, 0.0049 mole) in DMSO (4.9 ml) was stirred for 14 days in the presence of NMM (0.86 ml, 0.0078 mole). After diluting with water in the cold, the polypeptide was dialyzed using a 50 kD cut-off dialysis tubing changing the water daily for 15 days. The retentate was lyophilized to obtain 1.81 g of the $Ile^1$-polypentapeptide (yield: 88%). The carbon-13 NMR spectrum was obtained to confirm the structure.

Temperature Profiles for Coacervation

The temperature dependence for aggregation of the polypentapeptide is followed as the development of turbidity at 300 nm using a Cary 14 spectrophotometer. The sample cell is placed within a chamber vibrating at 300 Hz in order to facilitate equilibrium and to keep the aggregates from settling. The scan rate is 30° C./hour and the temperature was controlled with a Neslab ETP-3 programmer and monitored with an Omega 199A thermocouple monitor placed at the cell. The turbidity as a function of temperature provides a temperature profile for coacervation which is found to be concentration dependent. As the concentration is raised, the profile shifts to lower temperatures until further increases in concentration cause no further lowering of the temperature for aggregation. This defines the high concentration limit. The temperature for the onset of coacervation at the high concentration limit coincides with the temperature for the onset of the transition within the coacervate itself, even when there is no appreciable change in water content of the coacervate. The temperature for the midpoint of the temperature profile for the high concentration limit has been shown to correlate with the molecular weight of the polypentapeptide. When the midpoint is 25° C. for the PPP, the molecular weight is close to 100,000 daltons as calibrated by dialysis. For the $Ile^1$-PPP having a midpoint of 9° C., the molecular weight is greater than 50,000 daltons, as the synthetic polypeptide was retained by a 50,000 daltons dialysis membrane. The dialysis was carried out at 4° C. where the $Ile^1$-PPP is in solution.

Circular Dichroism Measurements

The circular dichroism studies were carried out on a Cary 60 spectropolarimeter equipped with a Model 6001 CD accessory modified for 330 Hz modulation of the left and right circularly polarized light. A concentration of 0.025 mg $Ile^1$-PPP/ml of doubly distilled water was characterized in a 10 mm path length cell. The low concentration was used to keep the size of the aggregate sufficiently small as not to cause light scattering distortions of the CD spectra. Even at this low concentration with this more hydrophobic polypentapeptide, above 35° C. the size of the aggregates was sufficient to cause particulate distortions as was apparent with the red shifting and dampening of the long wavelength negative band. The temperature was controlled and monitored from the cell as for the temperature profiles for coacervation.

Formation of the Elastomeric Matrix

In preparation for γ-irradiation cross-linking (the means of forming the elastomeric matrix), 130 milligrams of peptide $Ile^1$-PPP were dissolved in 220 milligrams of water in a cryotube. The sample was then shear oriented at 0° C. in a previously described pestle-cryotube arrangement. Gamma-irradiation was carried out at the Auburn University Nuclear Science Center at a dose rate of approximately 8,000 Roentgen/min and for sufficient time to achieve a $20 \times 10^6$ radiation absorbed dose (20 Mrad).

Thermoelasticity Studies

Thermoelasticity studies were carried out on a stress-stain instrument built in this Laboratory. The sample is mounted in two Delrin clamps. The top clamp is attached to a Statham UTC strain-gauge and the assembly is fixed. The bottom clamp is attached to a moving platform driven by a variable speed motor. Both clamps are enclosed in a thermostated water jacket. An inner chamber contains the solvent in which the elastomer is immersed which in this case is doubly distilled water. The sample was fixed in the top clamp and equilibrated in water at 60° C. for about an hour. The strain-gauge signal conditioner was balanced for zero force and the bottom clamp was attached to the sample. The sample was left to set overnight at room temperature. The bottom clamp was then adjusted for zero force and the distance between the clamps was measured. The elastomer was elongated to 40% extension at 5° C. and elastomeric force was then determined as a function of temperature. Equilibrium time to achieve constant force at a given temperature was typically twenty-four hours. Force measurements were made in 2° C. increments through the sharp rise in force and 5° C. increments at higher temperatures.

RESULTS

Temperature Profiles for Coacervation The $Ile^1$-PPP can be dissolved in water on standing below 8° C. On raising the temperature of the solution above 8° C., the solution becomes cloudy; on standing at the elevated temperature settling occurs and a viscoelastic phase forms in the bottom of the vial; on placing the vial in an ice bath the cloudiness immediately clears and the viscoelastic phase readily dissolves. Thus the $Ile^1$-PPP coaceravates when dissolved in water. The temperature profiles for coacervation (turbidity profiles) may be observed at different concentrations. As the concentration is raised, the temperature profile shifts to lower temperature. At 40 mg/ml, the high concentration limit (i.e, the lower concentration for which further increases in concentration cause no further lowering of the temperature for the onset of aggregation), the midpoint for the temperature profile for coacervation of $Ile^1$-PPP is 9° C.

Notably, the simple addition of a $CH_2$ to the 409 dalton repeating unit causes the onset of aggregation to shift to lower temperatures by 16° C. Observing that the curve for (0.1 mg Ile$^1$-PPP/ml) and that for (1.0 mg PPP/ml) are comparable with respect to the high concentration limits for each high molecular weight polymer suggests that the size of the aggregate for Ile$^1$-PPP is greater for a given concentration than it is for a comparable concentration of PPP. This will be relevant to comparisons made in the circular dichroism data.

Circular Dichroism

The circular dichroism curves were measured for Ile$^1$-PPP in water (0.025 mg/ml) at 2° C. and at 35° C. The low concentration was chosen in order that the size of the aggregate formed on association at 35° C. would have limited particulate distortions in the CD spectrum. At low temperature there is a large negative band near 195 nm. Such a negative band is characteristic of disordered proteins and polypeptides, though a standard value for this negative peak for complete disorder is $-4 \times 10^4$ rather than the observed value of $-1.2 \times 10^4$. Also the negative band near 220 nm, rather than zero ellipticity or a positive band which are taken is indicative of complete disorder, suggests elements of order at low temperature. The decrease in intensity of the negative CD band near 195 nm on raising the temperature of Ile$^1$-PPP in water indicates an increase in intramolecular order on raising the temperature, that is, there is an inverse temperature transition in an aqueous system. This indicates that hydrophobic interactions are developing as the ordered state develops. The intramolecular increase in order begins just above 0° C. and is complete by about 30° C. for a concentration of 0.025 mg/ml. The transition would have been complete at a lower temperature (the transition would have been sharper) if the CD data could have been obtained at higher concentration without significant particulate distortion. Experimentally it can be demonstrated that Ile$^1$-PPP and PPP have essentially identical conformations below the onset temperature for the transition and that they have essentially identical conformations after the transition is mostly completed. Thus while maintaining essentially identical conformations, which is assisted by the retention of β-branching, the addition of a CH$_2$ moiety lowers the transition toward increased order by about 15° C.

Characterization of Elasticity

The elastic (Young's) modulus determined for 20 MRAD cross-linked Ile$^1$-PPP coacervate was $4 \times 10^5$ dynes/cm$^2$ which is within the range of values obtained for 20 Mrad cross-linked PPP. The range of values is due to variable vacuolization occurring during γ-irradiation which makes difficult accurate measurement of cross-sectional area. It should be appreciated, however, that γ-irradiation causes no detectable polymer breakdown when measured by carbon-13 and nitrogen-15 NMR.

The temperature dependence of elastomeric force for an elastomeric band of Ile$^1$-PPP at 40% elongation is now considered. A near zero elastomeric force is measured at 8° C.; on raising the temperature there is a dramatic, an abrupt increase in elastomeric force. Full force is reached by 25° C. and becomes essentially constant with further increases in temperature. A similar dramatic rise in elastomeric force with increase in temperature is observed for 20 Mrad cross-linked PPP coacervate at 60% extension but this curve is displaced about 15° C. to higher temperatures. Using three different physical methods it can be shown that the addition of a CH$_2$ moiety (the replacement of Val by Ile) shifts the transition to lower temperatures by 15° C. without changing the conformation of the polypentapeptide before and after the transition. While the previously reported data on the naturally occuring PPP of elastin demonstrate a correlation of increased structural order with increased elastomeric force, the Ile$^1$-PPP data with the transition shifted by 15° C. appear to confirm an obligatory coupling of increased order with increased elastomeric force at fixed length.

In fact, the correlation of increased order with increased elastomeric force at fixed length is seen with the PPP. When the transition is shifted to lower temperatures, as in Ile$^1$-PPP, the development of elastomeric force faithfully shifts to lower temperatures. There appears in such elastomeric polypeptides to be a strict coupling between increasing order and increasing elastomeric force; and the molecular structure provides an understanding as to how this can occur. The similar conformations of PPP and Ile$^1$-PPP and the similar elastic moduli for the two polymers indicate that these do not appear to be factors in the evolutionary retention of $(VPGVG)_n$. What is now clear is that even the subtle addition of a-CH$_2$-moiety, for example, while having little effect on the stereochemistry of rather nonexacting, nonrestricting hydrophobic associations, has a significant effect on the thermodynamics. The larger clathrate-like cage of water surrounding the Ile side chain provides a greater ΔS as the more-ordered water surrounding the side chain becomes less ordered bulk water such that in the transition ΔH=TΔS at a lower temperature. By means of calorimetry, the ΔH for PPP has been estimated at 2 to 3 cal/gram which is approximately 1 kcal/mole of pentamers. Thus, the increase in entropy change need only be about 5% to cause the temperature of the transition to decrease about 15° C. from 298° K to 283° K. Utilizing known hydrophobicity scales for amino acids, the hydrophobicities given in a free energy of transfer scale of kcal/mole, are −4.10 for VPGVG and −5.38 for IPGVG. While the extent of the hydrophobicity that is utilized is expected to depend on the stereochemistry of the more-ordered polypeptide state, it would appear that not all of the total potential effect is actually realized.

The above-described hydrophobic effect upon transition temperatures is also supported by the elastin polytetrapeptide, $(Val^1-Pro^2-Gly^3-Gly^4)_n$. That is, it has also been discovered that high molecular weight PTP undergoes a reversible temperature elicited aggregation with an onset of aggregation at 48° C., rather than 24° C. as for high molecular weight PPP.

However, it has also been found that the inverse temperature transition for PTP is only complete at about 70° C. Moreover, this high temperature of transition appears to be explained by considering the lower hydrophobicity of PTP as compared to PPP.

For example, utilizing the Nazaki-Tanford and Bull-Breese hydrophobicity scales with the hydrophobicity of the Gly residue taken as zero, the free energy of transfer for the pentamer, VPGVG, would be −4100 cal/mole whereas that of the tetramer, VPGG, would be −2540 cal/mole. Thus, if hydrophobicity of the repeating unit is the determining factor, then the inverse temperature transition for the PTP would be at a higher temperature than that of the PPP. Furthermore if the inverse temperature transition (the increase in intramolecular order) is required for the development of elastomeric force, then the temperature dependence of elastomeric force of the PTP matrix would be expected to show a similar shift to higher temperature relative to that of the PPP matrix.

This inverse temperature transition is actually centered at near 50° C. for PTP, shifted some 25° C. higher than that of PPP. For Ile$^1$-PTP, it is shifted some 30° C. lower in temperature than that of PTP. Also, it has been found that the development of elastomeric force upon raising the temperature is similarly shifted about 25° C. higher for the PTP matrix (20 Mrad cross-linked) as compared to the PPP matrix (20 Mrad crosslinked).

Accordingly, in view of the above, it is now possible, by selecting the appropriate combination of PTP and PPP matrices or analogs thereof of the present invention to shift the transition temperature of a bioelastomer containing elastin PTP, PPP and analogs thereof and PHP over a range of about 75° C. Furthermore, wherever this transition would occur in the range of about −25° C. for Phe$^1$-PPP in water/ethylene glycol or about 50° C. for PTP, in water, for example, there is a large change in elastomeric force which accompanies a relatively small change in temperature.

Thus, it is now possible to provide bioelastomers having incorporated therein repeating units having decreased hydrophobicity, such as—(VPGG)$_n$—.

In particular, in accordance with the present invention, is also provided a bioelastomer containing elastomeric units comprising tetrapeptide, or pentapeptide or units thereof modified by hexapeptide repeating units and mixtures thereof, wherein the repeating units comprise amino acid residues selected from the group consisting of hydrophobic amino acid and glycine residues, wherein said repeating units exist in a conformation having a β-turn which comprises a tetrapeptide of the formula:

$$-X^3-(VPGG)_n-Y_3-$$

wherein
X$^3$ is PGG, GG, G or a covalent bond;
Y$^3$ is VPG, VP, V or a covalent bond; and
V is a peptide-producing residue of L-valine;
P is a peptide-producing residue of L-proline; and
G is a peptide-producing residue of glycine;
and n is an integer from 1 to 5,000, or n is 0, with the proviso that X$^3$ and Y$^3$ together constitute a repeating tetrameric unit in an amount sufficient to adjust the development of elastomeric force of the bioelastomer to a predetermined temperature.

Moreover, the materials of the present invention also further provides a bioelastomer containing elastomeric units comprising tetrapeptide, or pentapeptide or units thereof modified-by hexapeptide repeating units and mixtures thereof, wherein the repeating unit comprises amino acid residues selected from the group consisting of hydropholic amino acid and glycine residues, wherein said repeating units exist in a conformation having a β-turn which comprises
A) a polypentapeptide of the formula:

$$-X^1-(IPGVG)_n-Y^1-$$

wherein
X$^1$, Y$^1$, P, G, I, V and n are as defined above; and
B) a polypentapeptide of the formula:

$$-X^2-(VPGVG)_n-Y^2-$$

wherein X$^2$, Y$^2$, P, G, V and n are as defined above; or

C) a polytetrapeptide of the formula:

$$-X^3-(VPGG)_n-Y^3-$$

wherein X$^3$, Y$^3$, P, G, V and n are as defined above in relative amounts sufficient to adjust the development of elastomeric force of said bioelastomer to a predetermined temperature.

In accordance with the present invention are also provided PTP analogs, such as Ile$^1$-PTP, which are analogous to the various PPP analogs described above. In fact, any PTP-analog can be used in the preparation of the present bioelastomers which suffices to attenuate the hydrophobicity of the functional repeating unit, such as -(IPGG)-$_n$, while retaining the elasticity of the bioelastomer. Accordingly, in view of the principles set out above, one skilled in the art would, in view of this disclosure, be able to ascertain other PTP analogs which can be used advantageously in accordance with the present invention.

Thus, in accordance with the present invention is also provided a bioelastomer containing elastomeric units comprising tetrapeptide, or pentapeptide or units thereof modified by hexapeptide repeating units and mixtures thereof, wherein the repeating units comprise hydrophobic amino acid and glycine residues, wherein the repeating units exist in a conformation having a β-turn which comprises a tetrapeptide of the formula:

$$-X^4-(IPGG)_n-Y^4-$$

wherein
X$^4$ is PGG, GG, G or a covalent bond;
Y$^4$ is IPG, IP, I or a covalent bond; and
I is a peptide-producing residue of L-isoleucine;
P is a peptide-producing residue of L-proline; and
G is a peptide-producing residue of glycine; and
n is an integer from 1 to 200, or n is 0, with the proviso that X$^4$ and Y$^4$ together constitute a repeating tetrameric unit, in an amount sufficient to adjust the temperature of which the elastomeric force of the bioelastomer develops.

Of course, the materials of the present invention are bioelastomers having the above-recited structural features, but they may also have any combination of the repeating units -(IPGVG)-$_n$, -(VPGVG)-$_n$, -(VPGG)-$_n$, -(IPGG)$_n$ or other analogs thereof, such as Ala$^3$-PPP or Phe$^1$-PPP.

In fact, the present invention includes, in general, all bioelastomers containing elastomeric units comprising tetrapeptide, or pentapeptide or units thereof modified by hexapeptide repeating units and mixtures thereof, wherein the repeating units comprise hydrophobic amino acid residues and glycine residues, wherein the repeating units exist in a conformation having a β-turn which comprises a tetrapeptide or pentapeptide unit or repeating unit thereof, in an amount sufficient to adjust the development of elastomeric force of said bioelastomer to a predetermined temperature, with the proviso that the elasticity of the bioelastomer is retained.

However, in order to clarify the various aspects of the present invention relating to PTP, the following Examples and discussion are provided. Of course, the Examples are for purposes of illustration only and are not intended to limit the present invention.

EXAMPLES

Peptide Synthesis

General Approach: The synthesis of polytetrapeptide, $(VPGG)_n$, can be achieved using any of the following permutations as the starting tetramer unit: Val-Pro-Gly-Gly, Gly-Val-Pro-Gly, Gly-Gly-Val-Pro, or Pro-Gly-Gly-Val. The first sequence (VPGG) was used in this laboratory both with the pentachlorophenyl ester (OPcp) activation and with the p-nitrophenyl ester (ONp) activation methods, and the latter method yielded polymer of significantly higher molecular weight. In synthesizing the polypentapeptide, $(VPGVG)_n$, using different permutations of the pentamer unit with different activating groups for polymerization, it was observed that the pentamer having Pro as the C-terminal amino acid and -ONp for activation gave high molecular weight polymers. Similar results have been experienced in the case of the preparation of polyhexapeptide, $(VAPGVG)_n$. Hence, a similar approach was determined to be reasonable in the case of PTP also, i.e., sequence (GGVP) with -ONp activation. For comparison, H-VPGG-ONp, H-GVPG-ONp and H-GGVP-ONp were all tried for polymerization. As expected, the latter tetramer sequence gave a very high molecular weight polymer when determined by the TPτ studies and here is described the synthesis of this latter material as shown in the Scheme II. The sequence (PGGV) was not attempted because it has an optically active and bulky amino acid, Val, at its C-terminal.

resonance, thin-layer chromatography (TLC) and elemental analyses.

Details of Syntheses: Valine and Proline are of L•configuration. Boc-amino acids were purchased from Bachem, Inc., Torrance, Calif. HOBt was obtained from Aldrich Chemical Co., Milwaukee, Wis., and Bio-sil silica gel (200–400 mesh) was purchased from Bio-Rad Laboratories, Richmond, Calif. TLC plates were obtained from Whatman, Inc., Clifton, N.J. and the following solvent systems were used for determining the homogeneity of the products: $R_f{}^1$, $CHCl_3(C):MeOH(M):CH_3COOH(A)$, 95:5:3; $R_f{}^2$, CMA (85:15:3); $R_f{}^3$, CMA (75:25:3); $R_f{}^4$, CM (5:1). Elemental analyses were carried out by Mic Anal, Tuscon, Ariz. Melting points were determined with a Thomas Hoover melting point apparatus and are uncorrected.

Boc-Gly-Gly-OBzl (I): Boc-Gly-OH (17.52 g, 0.1 mole) in a mixture of $CHCl_3$ (50 ml) and acetonitrile (50 ml) was cooled to $-15°$ C. and EDCI (19.17 g, 0.1 mole) was added and stirred for 20 minutes. To this, a pre-cooled solution of H-Gly-OBzl•tosylate (37.1 g, 0.11 mole), NMM (12.09 ml, 0.11 mole) in $CHCl_3$(100 ml) was added and stirred overnight at room temperature. After removing the solvent, the residue was taken in $CHCl_3$ and extracted with acid and base. Chloroform was removed under reduced pressure, triturated with pet. ether, filtered, washed with pet. ether and dried to obtain 30.2 g of I (yield: 93.7%), m.p. 82°–83° C. $R_f{}^2$, 0.52; $R_f{}^4$, 0.82. Anal. Calcd. for $C_{16}H_{22}N_2O_5$: C, 59.61;

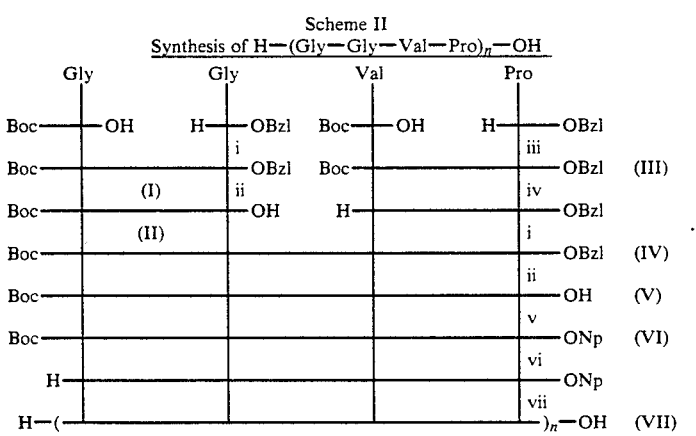

Scheme II
Synthesis of $H-(Gly-Gly-Val-Pro)_n-OH$ i) EDCI—HOBt;
ii) $H_2$—Pd/C;
iii) IBCF—HOBt;
iv) HCl/Dioxane;
v) Bis(p-nitropehnyl)carbonate;
vi) TFA;
vii) DMSO—NMM Boc-GG-OBzl (I) was prepared using EDCI for coupling and was hydrogenated to give the acid (II). Boc-VP-OBzl (III) was synthesized by the mixed anhydride method in the presence of HOBt, deblocked, and coupled with II using EDCI-HOBt to obtained Boc-GGVP-OBzl (IV). After hydrogenating to the acid, V, it was converted to -ONp (VI) by reacting with bis(p-nitrophenyl)carbonate. After removing the Boc-group, the active ester was polymerized, dialyzed against water using a 50,000 molecular weight cut-off dialysis tubing and lyophilized. The intermediate and the final products were checked by carbon-13 nuclear magnetic H, 6.88; N, 8.69%. Found: C, 59.43; H, 6.88; N, 8.35%

Boc-Gly-Gly-OH (II): I (10 g, 0.31 mole) in acetic acid (100 ml) was hydrogenated at 40 psi in the presence of 10% Pd-C catalyst (1 g). The catalyst was filtered with the aid of celite and solvent removed under reduced pressure. The residue was triturated with EtOAC, filtered, washed with EtOAc, pet. ether and dried to yield 6.3 g of II (yield: 87.5%), m.p. 118°–120° C. (decomp.). $R_f{}^2$, 0.28; $R_f{}^3$, 0.44. Anal. Calcd. for $C_9H_{16}N_2O_5$•$H_2O$: C, 43.19; H, 7.25; N, 11.19%. Found: C, 43.53; H, 7.40; N 10.90%.

Boc-Gly-Gly-Val-Pro-OBzl (IV): III (6.0 g, 0.0148 mole) (39) was deblocked with HCl/Dioxane and solvent removed under reduced pressure. The residue was triturated with ether, filtered, washed with ether, then pet. ether and dried. A very hygroscopic material was obtained (4.2 g, 0.0123 mole) which was coupled in DMF with II (2.86 g, 0.0123 mole) in the presence of 10% excess of EDCI (2.60 g) and HOBt (2.07 g). The reaction was worked up as described for I to obtain IV as a white foam in a quantitative yield, no sharp m.p. 54°–62° C. $R_f^2$, 0.42; $R_f^3$, 0.74. Anal. Calcd. for $C_{26}H_{38}N_4O_7$; C, 60.21; H, 7.38; N, 10.80%. Found: C, 60.0; H, 7.46; N, 10.81%.

Boc-Gly-Gly-Val-Pro-OH (V): IV (6.2 g, 0.012 mole) in acetic acid was hydrogenated and worked up as for II to obtain V quantitatively, no sharp m.p. 74°–83° C. $R_f^3$, 0.25; $R_f^4$, 0.15. Anal. Calcd. for $C_{19}H_{32}N_4O_7$: C, 51.10; H, 7.67; N, 12.54%. Found: C, 51.28: H, 7.50 N, 12.38%.

Boc-Gly-Gly-Val-Pro-ONp (VI): V (5.3 g, 0.0123 mole) in pyridine (30 ml) was reacted with bis(p-nitrophenyl)carbonate (5.64 g, 0.0185 mole). After removing the solvent, the residue was taken in $CHCl_3$ and extracted with acid and base. The peptide was chromatographed over a silica-gel column and eluted with 35% acetane in $CHCl_3$ after initially eluting with $CHCl_3$, to obtain 4.7 g of VI (yield: 69.2%), no sharp m.p. 74°–79° C. $R_f^2$, 0.76; $R_f^4$, 0.75. Anal. Calcd. for $C_{25}H_{35}N_5O_9 \cdot 1/2H_2O$: C, 53.75; H, 6.49; N, 12.53%. Found: C, 53.69; H, 6.44; N, 12.34%.

H-(Gly-Gly-Val-Pro)$_n$-OH (VII): VI (4.5 g, 0.0082 mole) in $CHCl_3$ (20 ml) was treated with TFA (35 ml) for 30 minutes and solvent removed under reduced pressure. The residue was triturated with ether, filtered, washed with ether, then with pet. ether and dried. The TFA salt (3.9 g, 0.0069 mole) in DMSO (7.6 ml) and NMM (1.22 ml, 1.6 equiv) was stirred for 14 days. After diluting with cold water, the polymer was dialyzed in a 50 kD cut-off dialysis tubing, changing water daily for 15 days, and the retentate was lyophilyzed to yield 1.65 g of the polytetrapeptide (yield: 77%). The carbon-13 NMR spectrum of the polymer was obtained and there were no extraneous peaks thereby verifying the synthesis and purity of the product.

Temperature Profiles for Coacervation

Polypeptide coacervation in water is reversible aggregation to form a new phase with a distinct composition. Association occurs on raising the temperature, disassociation on lowering the temperature. The process of coacervation was followed by monitoring the turbidity as a function of temperature using a Cary 14 spectrophotometer set at 300 nm, a Neslab ETP-3 temperature programmer with a 30° C./hour scan rate and an Omega 199A thermocouple monitor. The sample cell was placed in a vibrating chamber (300 Hz) to keep the aggregates from settling and to facilitate equilibrium. The temperature profiles for coacervation are concentration dependent. Dilution from a high concentration, after the high concentration limit is reached (approximately 40 mg/ml for high molecular weight elastomeric polypeptides), results in a shift of the turbidity profile to higher temperature.

Circular Dichroism Measurements

A Cary 60 spectropolarimeter equipped with a Model 6001 circular dichroism accessory with 330 Hz modulation of the left and right circular polarized beams was used to determine the circular dichroism patterns of 5 mg PTP in one ml of deionized-distilled (quartz immersion heater) water. Because of the smaller size or the relative transparency of the PTP aggregates (as with the cross-linked PTP matrix with a relatively small change in refractive index between solution and matrix) when compared to that of the PPP system, it was possible to use the 5 mg/ml concentration for the CD studies without being compromised by light scattering (particulate) distortions of the CD spectra. This is apparent from monitoring the negative band near 220 nm which becomes damped and red-shifted as the particulate distortions become significant.

Preparation of the Cross-linked PTP Matrix

The PTP was prepared for γ-irradiation cross-linking by dissolving 130 milligrams of the peptide in 220 milligrams of water in a cryotube. The material was shear oriented overnight at 40° C. in a previously described pestle-cryotube assembly. The sample was exposed to approximately 8,000 Roentgen/min γ-irradiation at the Auburn University Nuclear Science Center. Exposure was of sufficient time to achieve a $20 \times 10^6$ radiation absorbed dose (20 Mrad).

Thermoelasticity Measurements

Thermoelasticity studies were carried out on a stress-strain apparatus. Clamping of the sample in the holder was done in two stages to prevent damage to the material at the clamp edge. The sample was first gripped lightly with the top clamp, raised to 60° C. while submerged in water within the temperature jacket and allowed to equilibrate for about 2 hours. The measured force consisting of the weight of the sample and grips in water were set to zero. The bottom grip was then attached to the sample and both grips tightened to hold the sample firmly. The bottom clamp was driven as in a stress-strain measurement and stopped at 40% elongation. Force data were recorded in 5° C. steps starting at 70° C. and continuing to 40° C. where the force approached zero.

RESULTS

Temperature Profiles for Coacervation

The polytetrapeptide is soluble in water in all proportions below 40° C. On raising the temperature above 40° C. the solution becomes turbid; on standing settling occurs to form a dense viscoelastic phase called a coacervate. The process is readily reversible; on lowering the temperature cloudiness clears and coacervate readily redissolves. By following the turbidity as a function of temperature, temperature profiles for coavervation are obtained which are concentration dependent. As more concentrated solutions are used, the onset of turbidity occurs at lower temperatures until further increases of concentration cause no further lowering of the temperature for onset of turbidity. The lower concentration above which raising the concentration no further lowers the temperature for onset of turbidity is called the high concentration limit. For this high moelcular weight PTP the high concentration limit is 40 mg/ml as 100 mg/ml gives the same profile. Dilution from 40 mg/ml causes a shift to higher temperature for the onset. The midpoint for the high concentration limit of PTP is 49° C. whereas the value for the high concentration limit of PPP is 25° C. The decreased hydrophobicity of the tetramer results in a 24° C. increase in the temperature required to bring about the hydrophobic interactions attending aggregation.

Circular Dichroism

The CD spectra were measured at 40° C. and 65° C. for 5 mg/ml of PTP in water. At the lower temperature there is a negative band near 220 nm and a second negative band in the 195–200 nm range. This latter band is considered to be indicative of polypeptides with limited order as fully disordered polypeptides are considered to have a negative band near 195 nm with an ellipticity of $-4\times10^4$. The lower magnitude of the short wavelength negative band for PTP and the negative band near 220 nm indicate some order in the PTP at 35° C. On raising the temperature the short wavelength negative band decreases in magnitude indicative of a transition toward greater intramolecular order. Interestingly, its midpoint corresponds approximately to the midpoint in the temperature profile for coacervation for a comparable concentration. It is important to note for the PTP that the change in intramolecular order precedes the intermolecular interactions, i.e., begins at a substantially lower temperature than the aggregational process. Thus, the intramolecular ordering of the PTP is shifted to higher temperature due to the decreased hydrophobicity of the tetramer as compared to the pentamer.

Thermoelasticity Data

The temperature dependence of elastomeric force (thermoelasticity data) was measured for 20 Mrad cross-linked PTP at an extension of 40%. Very little elastomeric force was exhibited by this matrix below 40° C. As the temperature is raised above 40° C., however, the elastomeric force develops to a maximal value near 70° C. A 20 Mrad cross-linked PPP matrix exhibited a similar transition but at about 20° to 25° C. lower in temperature. The development of elastomeric force, just as the temperature dependence of coacervation and of ellipticity for the PTP, is shifted by about 25° C. from that of the PPP. These properties are a function of the hydrophobicity of the repeating unit. Of particular interest is the comparison of the ellipticity data for the PTP with the thermoelasticity for the PTP. The transition as followed by ellipticity, which is a measure of intramolecular order, begins in the range 35° to 40° C., and similarly the elastomeric force begins to develop just below 40° C. By both physical measurements the transition is essentially complete by 70° C. At a fixed length, there is a close parallel between increase in intramolecular order and increase in elastomeric force. As the aggregational intermolecular processes, followed by turbidity, do not become significant until nearly 50° C., it appears that the PTP matrix allows a delineation between intramolecular and intermolecular processes as related to origins of elastomeric force.

The structural features of PTP appear to be very similar to those of PPP. For example, it is clear that the same principles are operative as for the PPP. The Type II $Pro^2$-$Gly^3$ $\beta$-turn is the dominant secondary structural feature and the ordering process is that of an inverse temperature transition with the optimization of intramolecular hydrophobic interactions as the temperature is raised. The perspective is again an open helix with $\beta$-turn spacers between turns of the spiral and with the Val and Pro side chains providing the intramolecular hydrophobic contacts. The suspended segment will necessarily be shorter and the librational motion will be focused on the $Gly^4$-$Val^1$ peptide moiety. Based on the cyclic conformational correlate there will be approximately 4 tetramers per turn of PTP $\beta$-spiral as opposed to the approximately 3 pentamers per turn for the PPP $\beta$-spiral.

Effect of Repeat Unit Hydrophobicity

That the transitions toward increased elastomeric force are actually inverse temperature transitions dependent on the hydrophobicity of the constituent peptide is apparent from the direction of the shift of the transition on changing the hydrophobicity of the repeating unit. As the repeating unit becomes more hydrophobic, the temperature for the transition shifts to lower values. Using the Nozaki-Tanford-Bull-Breese hydrophobicity scale, the pentamer (VPGVG) would have a free energy for transfer of $-4100$ cal/mole whereas that for the tetramer (VPGG) would be $-2540$ cal/mole. For the transition $\Delta H=T\Delta S$, and for a given $\Delta H$ a higher temperature would be required if the hydrophobicity giving rise to $\Delta S$ were less. The data show that the decreased hydrophobicity of the tetramer requires a higher temperature for the transition than for the more hydrophobic pentamer. This finding is in accordance with the above-mentioned results obtained with $Ile^1$-PPP. When $(IPGVG)_n$, or $Ile^1$-PPP, is prepared, the $Ile^1$-PPP coacervates; it increases intramolecular order on increasing the temperature and the $Ile^1$-PPP matrix increases elastomeric force on raising the temperature but the transition is shifted to 9° C. The hydrophobicity for this pentamer, (IPGVG), is $-5380$ cal/mole. A comparison of the temperature of the transition for the three polypeptide elastomers and the hydrophobicities of the repeating unit. Not only is the direction of the shift correct but the magnitude of the shift is also approximately correct. It is clear that the inverse temperature transition giving rise to the intramolecular ordering and elastomeric force development is indeed proportional to the hydrophobicity of the repeating unit, and it is the intramolecular process utilizing hydrophobic interactions that is responsible for the development of elastomeric force.

Thus, the bioelastomers of the present invention can encompass a wide variety of functional repeating units in order to provide a wide variation in temperature of elastomeric force development.

For example, the present bioelastomers include those having any of the following repeating units as defined above:

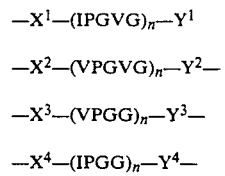

alone or in combination with each other in order to impart to the bioelastomer a capability of developing near maximum elastomeric force at a predetermined temperature.

However, also included in the materials of the present invention are all analogs of PPP and PTP and combinations thereof which modulate the hydrophobicity of the PPP and PTP repeating unit or units, without unduly interfering with either the formation of the viscoelastic phase or the librational motion of the polypeptide, i.e., the elasticity.

Other examples of such analogs and combinations thereof are such sequences as:

+IPGVG—Q—VPGVG+ₙ  +VPGVG—Q—VPGG+ₙ
+IPGVG—Q—VPGG+ₙ  +VPGVG—Q—IPGG+ₙ
+IPGVG—Q—IPGG+ₙ  +VPGG—Q—IPGG+ₙ where Q is either a direct covalent bond or an interspersing amino acid residue or residues, which can be any such residue which does not interfere with the elasticity of the polypeptide.

Of course, the repeating pentapeptide sequence, as well as the repeating tetrapeptide sequence can be widely substituted to modify the repeating unit hydrophobicity, as long as the elasticity of the bioelastomer is retained. For example, the incorporated pentapeptide repeating unit can be of the general formula:

$$+R_1PR_2R_3+_n$$

wherein $R_1$ is a peptide-producing residue selected from the group of Phe, Leu, Ile and Val; $R_2$ is such a residue selected from the group of Ala and gly; and $R_3$ is selected from the group consisting of Phe, Leu, Ile and Val; and n is an integer of from 1 to about 200; and wherein P is a L-proline-producing residue and G is a glycine-producing residue. Thus, "homopolymers" of the above tetrameric sequence can be utilized or "copolymers" of the above sequence can be used in conjunction with other repeating units in keeping with this invention.

Also, in general, tetrapeptide repeating units of the formula:

$$+R_1PGG+_n$$

can be utilized, wherein $R_1$ and n are as defined above for the pentameric sequences. These units are incorporated into the present bioelastomers in an amount sufficient to adjust the development of elastomeric force of the bioelastomer to a predetermined temperature.

Generally, in accordance with any of the bioelastomers of the present invention, the bioelastomers can be a "homopolymer" of a functional repeating unit, such as Phe¹-PPP, Ala³-PPP Ile¹-PPP, or Ile¹-PTP; or they can be a "copolymer" of the general formula $+S_a—T_b+$-n wherein either S or T constitutes a functional repeating unit designed to modify or shift the temperature of elastomeric force development of the bioelastomer, while either S or T, whichever is remaining, constitutes another repeating unit of the bioelastomer. As noted, such "copolymers" can be of either the block or random variety, which means that a and b can each be 1 or a larger integer.

Further, for these "copolymers", it is possible, as noted, that more than one functional repeating unit can be used to modify the temperature of elastomeric force development. Thus, both units —S— and —T— in the formula above would be such repeating units, for example, +IPGVG+ and +VPGVG+. Of course, each of S and T may be comprised of a subset of repeating units of $S_i$, $S_{ii}$ and $S_{iii}$. For example, three S subsets might be PPP analogs, such as (IPGVG), (FPGVG), where F is the one letter abbreviation for Phe, or (VPAVG).

Each one of the S or T repeating units is preferably incorporated within the molar range of 1-99%. More preferably still, is the incorporation of these units within the molar range of 5-95%. However, the actual molar content of any number of different repeating units is directly proportional to the desired transition temperatures using hydrophobicity scales.

The bioelastomeric material of the present invention may also contain PHP and variants thereof in order to accentuate modulus of elasticity and strength of materials produced containing these segments. This will now be described.

Additionally, as noted above, the natural hexapeptide and permutations of this sequence can be used to control the modulus of elasticity and tensile strength of artificial elastomers based on the polypenta- and polytetrapeptide sequences. Thus, the found that elastic modulus and tensile strength of the artificial bioelastomers of the type described herein can be increased by incorporating a segment of the formula $$—X—(APGVGV)_n—Y—$$

wherein

A is a peptide-forming residue of L-alanine;
P is a peptide-forming residue of L-proline;
G is a peptide-forming residue of glycine;
V is a peptide-forming residue of L-valine;
X is PGVGV, GVGV, VGV, GV, V, or a covalent bond;
Y is APGVG, APGV, APG, AP, A, or a covalent bond; and
n is an integer from 2 to 5,000 wherein this "hexameric" segment contains at least 18 amino acid residues, into an elastomeric peptide chain. In this way the modulus of elasticity and tensile strength can be readily increased.

The bioelastomeric polypeptide chains containing hexapeptide repeating units can be synthesized using any of the hexapeptide "monomers" that are permutations of the basic sequence. Thus, polymers generally will have the structure $B^1$(hexapeptide repeating unit)$_n$-$B^2$ where $B^1$ and $B^2$ represent the remainder of a peptide chain which is discussed later in detail. In fact, if the peptide polymer is not synthesized using hexapeptide "monomers" but rather is synthesized by sequential adding of amino acids to a growing peptide (such as in an automatic peptide synthesizer) the designation of a repeating unit is somewhat arbitrary. For example, the peptide H-V(APGVGVAPGVGVAPGV-GVAPGVGV)A-OH can be considered to consist of any of the following repeating units and end groups: H-(VAPGVG)₄-VA-OH, H-V-(APGVGV)₄-A-OH, H-VA(PGVGVA)₄-OH, H-VAP-(GVGVAP)₃-GVGVA-OH, H-VAPG(VGVAPG)₃-VGVA-OH, or H-VAPGV-(GVAPGV)₃-GVA-OH.

Synthesis of the elasticity-modifying hexameric segment (which is incorporated into the final elastomeric peptide) is straight-forward and easily accomplished by a protein chemist or using standard methods of microbial fermentation with recombinant DNA. The resulting intermediate peptides generally have the structure $B^3$-(repeating unit)$_n$-$B^4$ where $B^3$ and $B^4$ represent any chemically compatible end group on the amino and carboxyl ends of the molecule, respectively, and n is an integer from 1 to about 5,000. When $B^3$ is H, $B^4$ is OH, and n = 1, the compound is the hexapeptide itself. When n is greater than 1, the compound intermediate is a polyhexapeptide. It is possible that one or more amino acid residue or segment of amino acid residues not present in the normal hexapeptide sequence may be interspersed within a polyhexapeptide portion of an elastomeric polypeptide chain. As clearly indicated by the previous general formula and by the following discussion, the invention encompasses incorporation of a hexamer or polyhexapeptide into a larger peptide chain.

Other examples of terminal $B^3$ and $B^4$ end groups for the intermediate hexameric segment that is to be incorporated into the elastomeric polypeptide chain include portions of the repeating peptide units themselves with free amino or carboxylic acid groups or salts thereof, free amino or carboxylic acid groups or salts (especially alkali metal salts), and peptide or amino acid units that have retained a blocking group that was present during synthesis of the polypeptide or that have a biocompatible group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule.

The first product obtained in the synthesis of a hexapeptide monomer that is typically produced in the process of preparing a hexapeptide segment is a protected hexapeptide, such as Boc-L•Val-L•Ala-L•Pro-Gly-L•Val-Gly-OBzl. This protected monomer is converted into a reactive monomer that can be incorporated into a peptide chain by, for example, replacement of the benzyl ester with the p-nitrophenyl ester, for example by effectively exchanging with p-nitrophenyl trifluoroacetate or bis-(p-nitrophenyl)carbonate, and removal of the Boc protecting group. The resulting reactive monomer is polymerized, in the presence of a base such as triethylamine or N-methylmorpholine as necessary, to give a polypeptide containing hexamer units. Copolymerization with a reactive penta- or tetrapeptide as described herein gives the final bioelastomer of controlled elasticity. Alternately, intermediate hexapeptide segments can be independently synthesized and incorporated into a block copolymer also containing elastomeric units as described below. A blocking group, such as H-Val-OMe may be added at the conclusion of the polymerization reaction to convert the remaining reactive p-nitrophenyl esters to non-reactive terminal groups if desired.

The elasticity-modifying hexapeptide segments are believed to operate much in the same way as the hard segments in segmented polyurethanes. For example, when the polyhexapeptide, specifically $(VAPGVG)_n$, is dissolved in water at 4° C. and the temperature is raised, aggregation occurs over a relatively narrow temperature range and that range shifts to lower temperatures as the concentration is raised. The aggregation of the polyhexapeptide, in contrast to that of the polypentapeptide, is irreversible in water. The aggregates can be redissolved in trifluoroethanol-water mixtures and lyophilyzed to regain water solubility; i.e., the heat-illicited aggregation of the polyhexapeptide is not a true irreversible process. This is thought to be due to more rigid structure of the polyhexapeptide wherein on association there is an interlocking of hydrophobic ridges. Thus, in a copolymer comprising repeating hexapeptides and repeating pentapeptides, it appears that the hexapeptide repeats tend to associate selectively (i.e., to cluster) and that these clusters of stiffer hexapeptide units, separated by softer polypentapeptide or polytetrapeptide segments, impart additional rigidity to the composite material and result in an increased modulus of elasticity and increased tensile strength. This is quite analogous to the hard and soft segments of segmented polyurethanes, such as are described in Ulrich et al, in Synthetic Biomedical Polymers: Concepts and Applications, Szycher and Robinson, Eds. Technomic Publishing Co., Inc., West Port, Conn., 29-38 (1980).

Investigations have demonstrated that polyhexapeptide-polyhexapeptide interactions can occur within a predominantly polypentapeptide matrix. This is demonstrated by an increased elastic modulus which is consistent with a hard-segment role for the synthetic elastomeric polypeptide material. The results are also consistent with an interlocking by means of interdigitating hydrophobic ridges of repeating hexapeptide units. Preferred materials containing the hexameric segments of the invention would have the general formula $(E_mH_n)_p$, in which E represents an elastomeric tetrapeptide or pentapeptide unit and H represents a hexapeptide unit. Particularly preferred are polymers in which m is an integer from 1 to 100 (preferably 3 to 25), n is 3 or greater (preferably 5 to 10 and $\leq m$), and p is of such a magnitude to provide a single polypeptide sequence having 50-5000 residues, preferably 500-2000 residues (preferably p=10 to 100). It should be noted that the formula $(E_mH_n)_p$ does not necessarily represent a block copolymer, unless so specified, but can also represent a random copolymer having the indicated ratios of repeating units, wherein groups of at least three sequential hexamers are present in a random fashion. Typically, the ratio of elastomer unit to hexameric unit is from 1:1 to 10:1.

Biocompatibility tests have been conducted in rabbits on the polypentapeptide and on γ-irradiation cross-linked polypentapeptide. The material was found to be biocompatible and to be biodegradable. Because of the similarity of the polyhexapeptide sequences, a material incorporating hexapeptide sequences as described herein should have these same characteristics.

The amount of hexapeptide incorporated into a polypentapeptide or polytetrapeptide elastomer of the invention will naturally vary according to the desired modulus of elasticity and tensile strength. Incorporation of a small relative amount of the hexapeptide will result in a small increase in the elastic modulus and tensile strength while introduction of a larger proportion will result in a larger increase. Accordingly, the amount necessary to produce any increase in elastic modulus can readily be determined by simple experimentation. However, in order to retain sufficient elasticity of the resulting copolymer for biomedical applications, the ratios previously described are preferred.

The elastomeric units used with the hexapeptide segments to form the complete bioelastomer have been described above, including the U.S. patents and co-pending applications incorporated by reference. An essential feature of the elastomeric pentapeptide, tetrapeptide, and D-amino-acid-containing tetra- and pentapeptide elastomeric units of the earlier inventions is the existence of a sequence of regularly recurring β-turns which are characterized by a ten atom hydrogen bonded ring of the following formula:

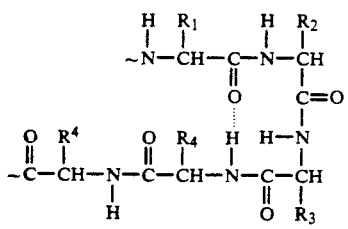

In this formula, $R_1$ through $R_5$ represent the side groups of the respective amino acid residues.

The spiral structures produced by a series of $\beta$-turns are more open than the more common $\alpha$-helix. As a result, the atoms between the atoms that participate in hydrogen bonding have a relatively greater freedom of movement, more so than in an $\alpha$-helix. This is particularly true of librational motions involving non-hydrogen bonded peptide moieties in the $\beta$-spiral. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in a motional restricting hydrogen bonding to other parts of the molecule or to other peptide molecules. Otherwise a greater energy barrier to the libration exists and motion will be restricted. Since non-hydrogen-bonded segments having freedom of motion exist in the $\beta$-spiral between the points of hydrogen bonding for the $\beta$-turns, these segments may be said to be librationally suspended with librational capabilities. Librationally active suspended segments therefore are a structural feature that exists in the elastomeric polymer because of the repeating $\beta$-turns with relatively infrequent hydrogen bonding.

Another factor leading to the high librational freedom of such molecules is the absence of polar interactions between the amino acid residues, either intrachain or interchain, other than the previously mentioned hydrogen bond. The amino acid residues present are generally all hydrophobic or glycine and accordingly do not exert significant forces on one another through space. If charged or polar groups were present, electrostatic interactions could limit librational freedom and restrict the number of available states in the relaxed (non-extended) form of the molecules and would shift the temperature of the inverse temperature transition. Polar and charged amino acid residues are not strictly prohibited, however, if their presence does not destroy the elasticity of the polypeptide molecule as a whole. For example, an occasional serine residue is present in the polypentapeptide sequence of naturally occurring porcine tropoelastin without destroying elasticity. Accordingly, hydrophobic amino acid residues and glycine are preferred in forming elastomeric polypeptides of the present type although other amino acids may be present to a small extent.

The size of the repeating unit of the elastomeric component is important in determining the stability and dynamic properties of the $\beta$-spiral. Repeating units having fewer than four or more than five amino acid residues can form $\beta$-spirals having the required librational motions when using a polynona-sequence comprised of a pentamer and a tetramer. Thus, elastomers of the present type appear to be limited to polypeptides having tetrapeptide or pentapeptide repeating units in the elastomeric component or perhaps having a regular combination of pentamer plus tetramer to afford a polynonapeptide. Elastomers containing an amino acid residue of opposite chirality at position three, as disclosed in U.S. Pat. No. 4,500,700 and discussed briefly below, are also believed to be limited to polypentapeptides or polytetrapeptides, with polypentapeptides being particularly important.

Selective replacement of glycine residues at position 3 in the elastomeric repeating units with hydrophobic D-residues gives an elastomer having a higher modulus of elasticity. Studies of the dominant conformational feature of the polypentapeptide of elastin, the Type II $Pro_2$-$Gly_3$ $\beta$-turn previously discussed, indicate that a D-residue at position three will stabilize the $\beta$-turn. Substituting a D-amino acid residue for the $Gly_3$ residue produces an elastomeric molecule (after cross-linking) having an elastic (Young's) modulus approximately twice that obtained for the corresponding molecule having a $Gly_3$ residue.

When a repeating unit having an amino acid residue of opposite chirality is utilized, it is preferred that the amino acid residue in position three be a hydrophobic D-amino acid although other D-amino acids are also contemplated to be within the scope of the present materials. Amino acid residues having no more than 10 carbon atoms in their amino acid side chain are preferred. Preferred hydrophobic side chains are alkyl, aryl, and arylalkl, where aryl represents a phenyl or alkyl-substituted phenyl group. Particularly preferred are the residues of D-alanine, D-valine, D-leucine, D-isoleucine, D-phenylalanine, D-2-aminobutanoic acid, and other molecules of similar size, polarity, and chirality. Especially preferred are alkyl side chains having 1-5 carbon atoms in an $\alpha$-amino acid residue having an $\alpha$-hydrogen.

The choice of individual amino acids from which to synthesize the remaining sections of the elastomeric repeating units and resulting polypeptide is unrestricted so long as the resulting structure comprises librationally suspended segments in a spiral. The amino acids are not restricted to $\alpha$-amino acids, although these are preferred, since it has recently become possible to predict the occurrence of $\beta$-turns from the $\alpha$-amino acid sequence of a polypeptide. A review article discussing the prediction of protein conformation, including the prediction of $\beta$-turns, was published by Chou and Fasman, *Ann. Rev. Biochem.*, 47, 251 (1978), which herein incorporated by reference. The size of the side chains present in the hydrophobic amino acids does not greatly affect the $\beta$-spiral since the side chains generally extend outward from the surface of the spiral with some important but non-restrictive interturn hydrophobic interactions. However, in order to minimize interchain interactions, it is preferred that the side chain contain no more than 10 carbon atoms. Preferred hydrophobic side chains are the same as those previously described for position three. In addition, it appears from the studies leading to the present invention that preferred side chains of the amino acids are hydrogen or hydrocarbon chains having 1-7 carbon atoms. Examples of especially preferred residues are glycine and the naturally occuring L-amino acids alanine, valine, leucine, and isoleucine as well as closely related molecules such as 2-methyl-2-aminopropanoic acid, L-2-aminobutanoic acid, and L-2-methyl-2-aminobutanoic acid, although it is preferred that the α-carbon have an α-hydrogen. Proline is also a preferred amino acid.

Given positions of the repeating units of the elastomeric component have amino acid residues that are particularly preferred. The first amino acid residue is preferred to be valine, leucine, or isoleucine; the second is preferred to be proline; the third has been previously discussed; the fourth is preferred to be valine, leucine or isoleucine; and the fifth residue is preferred to be glycine.

An elastomeric component consisting entirely of repeating units in which the third amino acid residue is of opposite chirality, as described herein, has an elastic modulus approximately twice that of an otherwise identical polypeptide in which all the amino acids have the same chirality, such as those described in U.S. Pat. No. 4,187,852. Accordingly, it is possible to easily alter the elastic modulus by using a mixture of monomers and controlling the amount of crosslinking between adjacent peptide chains. Elastic modulus is proportional to the number of crosslinks, although not in a strictly linear fashion. It should be noted that the modification of elastic modulus described above by using amino acid residues of opposite chirality operates by an entirely different mechanism from that of the present materials.

Because of the chirality of amino acids and of polypeptides produced therefrom, an equally effective polypeptide can be produced by using polypentapeptide repeating units in which all of the amino acids having chiral centers are of the opposite chirality from that ptevíously described: i.e., L-amino acid residues are replaced with D-amino acids. Since both L- and D-amino acids are available commercially and can be used as starting materials in a synthesis of the polypeptide of the invention, for example in the method disclosed later, either of these species of the invention may be easily produced. However, since D-amino acids are relatively more expensive, the more preferred species is that in which all or most of the amino acid residues of the elastomeric component are derived from L-α-amino acids and only the residue at position 3 is derived from a D-amino acid.

Methods of preparing elastomeric components in which the third position is occupied by a glycine residue have been disclosed in Rapaka and Urry, Int. J. Peptide Protein Res., 11, 97 (1978), Urry et al, Biochemistry, 13, 609 (1974), and Urry et al, J. Mol. Biol., 96, 101 (1975), which are herein incorporated by reference. The synthesis of these peptides is straightforward and can be easily modified to allow production of any polymer described in this application, if desired. The following summary, which is not to be considered limiting, is an example of one general method of synthesizing the polypeptides.

The first step in the formation of the elastomeric copolymer of the invention usually is synthesis of the various peptide monomers. Any of the classical methods of producing peptide molecules may be used in synthesizing the building blocks of the polymers of the present materials. For example, synthesis can be carried out by classical solution techniques starting from the C-terminal amino acid as a benzyl ester p-tosylate. Each successive amino acid is then coupled to the growing peptide chain by means of a water-soluble carbodiimide and 1-hydroxybenzotriazole. A typically used carbodiimide is 1-(3-dimethylaminopropyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The structure, examples of synthesis, and use of these elastomeric compounds and of various compositions containing these compounds is fully disclosed in the incorporated patent applications. The present material is not related to these elastomeric components themselves but uses them in the formation of the total elastomeric material containing the tetrameric, pentameric and hexameric segments for the prevention of adhesion.

Synthesis of the final elastomeric polypeptides containing the elastomer component and elasticity-modifying hexapeptide component of the present invention is straightforward and easily accomplished by a protein chemist. See, for example, the techniques described in Li and Yamashiro, J. Amer. Chem. Soc., 92, 7608–7609 (1970) which is herein incorporated by reference. The resulting generally polypeptides have the structure X-[(elastomeric unit)$_m$ (hexameric unit)$_n$]$_p$-Y where X and Y represent any chemically compatible end group on the amino and carboxyl ends of the molecule, respectively, and m, n, and p are as previously described. Block copolymers are preferred, although random copolymers are also suitable. Block copolymers can be synthesized sequentially in an automatic peptide synthesizer or by reacting preformed units consisting of activated elastomeric and hexapeptide units (which is preferred) or even by microbial fermentation. If the reaction with preformed units is used, it is preferred to use a shear stirring technique to orient the linear elastomeric units and to use EDCI as an activator. Relatively long reaction times and replenishment of EDCI during the course of reaction are preferred. Particularly preferred are polypeptides having molecular weights greater than 10,000 daltons, even greater than 100,000 daltons. It is possible that one or more amino acid residue or segment of amino acid residues (such as the crosslinking segments later discussed) may be interspersed within the polypeptide chain so long as the elasticity and biocompatibility of the resulting molecule is not completely disrupted. Examples of terminal end groups that can be present in bioelastomers of the invention include the repeating peptide units themselves with free amino or carboxylic acid groups or salts thereof and peptide or amino acid units that have retained a blocking group that was present during synthesis of the polypeptide or that have a blocking group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the β-turn conformation of the elastomeric component and does not negate biocomptability and that allows a suitable rtae of degradation for the molecule as a whole.

It is preferred that a bioelastomer containing elastomeric and hexapeptide repeating units be heated in order to kinetically drive the molecules to form hexamer-hexamer interaction. By heating the material, the hexamer segments are driven together in interlocking as described above. When the products are cooled, insufficient kinetic energy exists to unlock the interlocked hexamer-hexamer segments.

The temperature to which the sample is raised in order to effect this heat treatment can readily be determined for a particular copolymer in at least two ways. First, elastic modulus can be measured as a function of temperature in a small sample of the copolymer product. There is a rapid increase in modulus of elasticity at the temperature at which the hexamer-hexamer interactions begin to occur. Alternatively, turbidity measurements provide the same information. Opacity of the samples indicates interlocking of the hexamer regions.

The bioelastomers of the invention are quite stable to heat treatment. For example, a polypentapeptide (lacking the hexamers of the present invention) can be heated for 24 hours at 80° C. without degradation. The polyhexapeptide is even more stable to heat degradation. Bioelastomers of the invention can be autoclaved, thereby sterilizing the bioelastomer while providing the increased modulus of elasticity and tensile strength at the same time.

When bioelastomers of the invention are heat treated, it is preferred that this treatment take place prior to any of the cross-linking processes described later.

In addition to having an increased modulus of elasticity, bioelastomers incorporating PHP also show an increased tensile strength and thus a greater resistance to tearing than bioelastomers prepared solely from the elastomeric units described in this specification.

An improved prosthetic material of higher tensile strength can be produced by using a collagen-like load bearing component in addition to an elastomeric component of the correct elastic modulus. This can be achieved by compounding the synthetic elastomeric high polymers described above to a second material with greater strength. The second material forms the core of the composite fiber and will be referred to as the "collagen analogue" or "core fiber". The term core fiber is not limited to those forms of elastomeric composite materials in which a first fiber is coated with a second material, but also refers to other forms in which a strength giving fiber (the core fiber) is chemically bonded to a second component that is elastomeric (the polypeptide). For example, elastomeric polypeptide fibers may form strands between the segments of a crimped core fiber. The essential feature is that a chemical bond (of any type) exists between the surface of the core fiber and the elastomeric polypeptide so that the two components do not become separated while the elastomeric component is being stretched or is reforming the relaxed $\beta$-spiral. The chemical bond may be covalent or ionic bonding, hydrogen bonding, or the result of electrostatic interactions of various types, such as ion-dipole and diopole-dipole interactions. Covalent bonding is preferred. Linkages may be formed in any conventional manner and, if covalent bonds are to be formed, they can be accomplished by reacting a functional group of the polypeptide with a functional group of the core fiber. The functional groups may be present naturally as part of the polypeptide or core fiber or may be formed later, for example, by suitable chemical reactions involving the already formed core fiber or polypeptide. Composite materials of this type are fully described in U.S. Pat. No. 4,474,851, which is herein incorporated by reference.

It is generally desirable to cross-link the molecules of the polypeptide prior to use in vivo in order to increase its strength and elasticity. If a composite fiber is being formed, it is preferred to perform the cross-linking after the polypeptide has adhered to the core fiber. The method of creating the linkage is not limited to the methods disclosed in this application and may be any method of covalent or non-covalent linkage that does not prevent the elastomeric copolymer or the composite fiber from behaving as an elastomer. Suitable methods and types of linkages include cross-linking with ionizing irradiation and chemical modification or substitution of amino acid residues of the peptide repeating units and of the collagen analogue repeating units in order to form reactive side groups that undergo chemical reaction with each other (chemical cross-linking) e.g., by amide linkage, aldol condensation, Schiff base formation, enzymatic cross-linking by lysyl oxidase, or ester formation or even disulfide bridge formation. Another suitable method of cross-linking comprises the use of photoactivated agents such as those giving rise to carbenes or nitrenes which may be attached as amino acid side groups or introduced as separate diffusible molecules.

A particular type of chemical cross-linking occurs when polypeptides are prepared in which some of the repeating units are replaced by units in which one of the amino acid residues is replaced by the residue of an amino acid that has a reactive side chain. For example, it is possible to prepare a first batch of polypeptide in which a residue of some of the repeating units is replaced by an amino dicarboxylic acid, such as aspartic or glutamic acid, and a second batch of polypeptide in which a residue of some of the repeating units is replaced by a diamino carboxylic acid, such as lysine or ornithine. After a mixture of these two batches has been formed into a sheath around the core fiber, the free amino and carboxylic acid side group are allowed to react to create the cross-linkages. Formation of cross-linked polypentapeptide produced in this manner is described in U.S. Pat. No. 4,187,852, which is herein incorporated by reference. If chemical cross-linking is used, it is also necessary to provide reactive functional groups in the core fiber so that linkages between the peptide elastomer and the core fiber will also occur. Such modifications are well understood by polymer chemists and may include, for example, glycidyl esters of acrylates or methacrylates (as examples of reactive groups present during formation of the core polymer), or amino or carboxylic acid groups added to the terephthalic acid moiety of Dacron (as examples of reactive groups formed after formation of the core fiber).

The degree of cross-linking is such that elastomeric properties are imparted to the resulting composite fiber and can be varied to provide the desired dynamic mechanical properties. Preferred is an average of one cross-link for every 5 to 100 elastomer repeating units with 10 to 50 being most preferred. The degree of chemical cross-linking can be controlled by selecting the proper proportions of reagents. In general, the ratio of repeating units with reactive side groups to unmodified repeating units within a single molecule can vary from 1:1 to 1:20 with a ratio of about 1:5 being preferred. When two batches of polypeptide containing carboxylate or amino side groups as described above are used, the ratio of carboxylate-side-group-containing polypeptide to amino-side-group-containing polypeptide can vary from 4:1 to 1:4 with a ratio of about 1:1 being preferred.

An additional method of chemical cross-linking using cross-linking units capable of being cross-linked by lysyl oxidase is described in U.S. Pat. No. 4,589,882.

When irradiation cross-linking is performed, a satisfactory approach is irradiation with gamma radiation from a cobalt-60 source. Other radiation energies required to provide a cross-linking action without excessive destruction of the core fiber or elastomeric peptide structure may be easily determined by simple experimentation. The degree of cross-linking is determined by the length of time and energy of the irradiation when irradiation cross-linking is performed. At least two cross-linkages per molecule are needed. The number of cross-linkages per molecule and the elastic modulus increase as the radiation dose increases. The requisite time for any desired amount of cross-linking is easily determined by simple experimentation for any given source of irradiation energy. Samples of non-cross-linked polymer or composite fiber are exposed to the source of ionizing energy for varying lengths of time, and the resulting elastic modulus is measured. In this manner the irradiation time required to produce an elastic modulus necessary to match a specific design characteristic of the polymer or composite fiber can easily be determined.

The materials of this invention, as noted, are advantageously used as materials for the protection of wound sites, whereby adhesion to a second site is prevented. However, these materials can also be incorporated into regenerating tissue, such as an artificial vein or artery or artificial skin or ligaments. As already noted, the present materials may also be advantageously used in the protection of burn areas.

The above disclosure generally describes the present invention. A more complete understanding can be obtained by reference to the following specific examples, which are provided herein for purposes of illustration only and are not intended to be limiting unless otherwise specified.

EXAMPLE

Abbreviations: BOc, tert-butyloxycarbonyl; Bzl, benzyl; DMSO, dimethylsulfoxide; EDCI, 1-(3-dimethylaminopropyl)-3-ethylcarbodiimide; HOBt, 1-hydroxybenzotriazole; IBCF, isobutylchloroformate: NMM, n-methyl morpholine; ONp, p-nitrophenylester; TFA, trifluoracetic acid; A, alanine; G, glycine; V, valine; P, proline; PPP, polypentapeptide (VPGVG)$_n$; PHP, polyhexapeptide (VAPGVG)$_n$ and P(HP)P, cosequential polyhexapentapeptide.

EXPERIMENTAL DETAILS

Peptide Synthesis

The synthesis of the sequential polypeptides of the hexapeptide sequence, Boc-(VAPGVG)$_n$-OCH$_3$ where n=2, 3, and 4 was carried out by classical solution methods as shown in Scheme III.

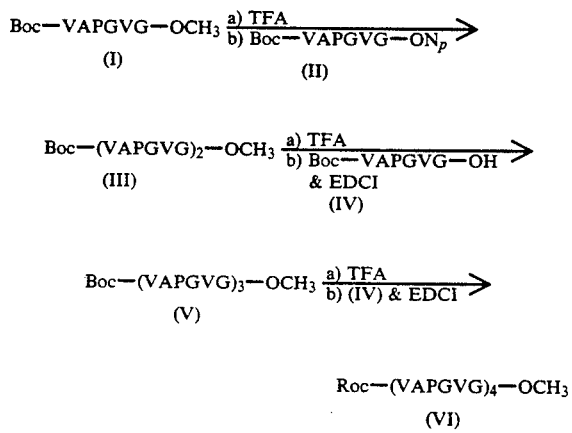

Scheme III
Synthesis of the Sequential Polypeptides of the Hexamer Sequence was deblocked with TFA and coupled with Boc-VAPGVG-ONP (II) in the presence of HOBt to obtain Boc-(VAPGVG)$_2$-OCH$_3$ (III). After deblocking III, it was coupled with Boc-VAPGVG-OH (IV) using the water soluble carbodiimide, EDCI, to obtain the next higher homologue V. Similarly Boc-(VAPGVG)$_4$-OCH$_3$ (VI) was also obtained. The syntheses and purity of the oligohexapeptides with n=2 and 3 have been verified by C-13 NMR.

The synthesis of the polyhexapeptide, H-(VAPGVG)$_n$V-OCH$_3$ has been carried out starting from the monomer sequence H-VAPGVG-ONp. Recently, it was observed in the case of the preparation of the PPP, that with the permutation where Pro is present as the C-terminal amino acid in the monomer sequence, as H-GVGVP-ONp instead of H-VPGVG-ONp, a very high molecular weight polymer (about 100,000 dalton) could be obtained Urry et al., in *Biocompatibility of Natural Tissues and Their Synthetic Analogues* (D. F. Williams, Ed.) CRC Press, Inc., Boca Raton, Fla., 89–116 (1985). Hence a similar approach was taken for the preparation of the polyhexapeptide with Pro as the C-terminal amino acid in the monomer sequence. The synthesis of poly(GVGVAP)-OH is shown in Scheme IV. The product may, of course, also be written H-GVG(VAPGVG)$_n$VAP-OH.

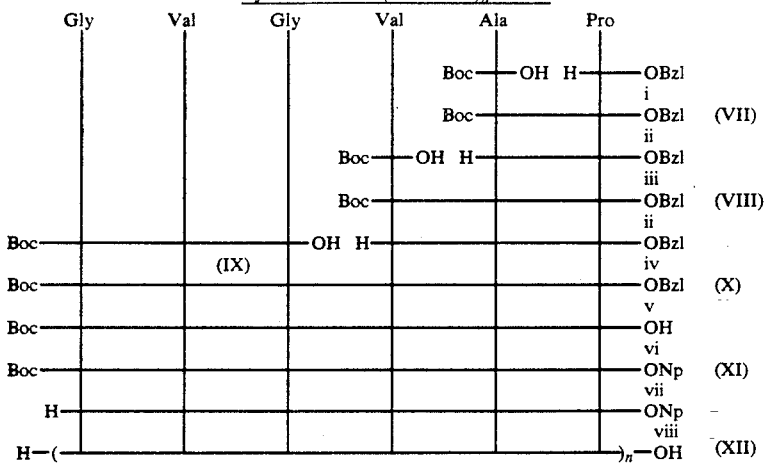

i) IBCF—HOBt;
ii) HCl/Dioxane;
iii) IBCF;
iv) EDCI—HOBt;
v) H$_2$—Pd/C
vi) Bis-(p-nitrophenyl) carbonate;
vii) TFA;
viii) DMSO—NMM Boc-AP-OBzl (VII) was prepared by the mixed anhydride method in the presence of HOBt. After deblocking, the coupling was carried out with Boc-Val-OH to obtain the tripeptide benzyl ester (VIII) which was deblocked and coupled with Boc-GVG-OH (IX) to obtain the hexapeptide, X. Following hydrogenolysis, the peptide acid was converted to the p-nitrophenyl ester (XI) using bis(p-nitrophenyl) carbonate. After removal of the Boc group with TFA, a one-molar solution of the active ester in DMSO was polymerized for 14 days in the presence of 1.6 equiv. of NMM. On diluting with water the PHP was dialyzed against water, first using 3,500 molecular weight cut-off dialysis tubing for 7 days and then 50,000 M.Wt. cut-off tubing for 7 more days and finally the retentate was lyophilized.

Random copolymerization of hexa and pentapeptides: The active p-nitrophenylesters of the hexapeptide, H-GVGVAP-ONp, and the pentapeptide, HGVGVP-ONp, were mixed in the desired ratio (1:2) and polymerized in the usual way. The product is a sequential polypeptide in which in a single chain there is presumably a random mixture of hexapeptides and pentapeptides in a 1:2 ratio. This product will be called a cosequential polyhexapentapeptide and will be abbreviated as P(HP)P. The purity of the intermediate and final compounds was checked by thin layer chromatography, elemental analyses and nuclear magnetic resonance. Synthesis and purity of the polyhexapeptide, PHP, the cosequential polyhexapentapeptide, P(HP)P, and for comparison of the polypentapeptide, PPP, have been verified by C-13 NMR.

Temperature profiles of aggregation: Temperature profiles of aggregation (turbidity profiles) were obtained with a Cary 14 spectrophotometer set at 300 nm to follow light scattering as a function of increasing temperature. The heating rate was 30° C. per hour and to insure appropriate mixing of the polymers the sample cell was equipped with a 20 KHz vibrator. Samples were run in duplicate with fresh material used each time in a 1 mm rectangular cell with a total volume of 0.3 ml.

Reversibility of the polypeptides was checked immediately after each temperature run by exposing the sample to an ice bath for 30 minutes. If the aggregation was not reversible, the sample was further incubated at 4° C. for 16 hours. For the oligohexapeptides, reversibility was checked after the sample had been taken to 72° C. where n=3 and to 60° C. where n=4 and then when both had been taken to 80° C.

Preparation of polyhexapeptide sheet from trifluoroethanol: The polyhexapeptide (PHP) was evaporated from trifluoroethanol (TFE) in a round bottom flask after which ether was added, and the resulting PHP sheet was removed. This material was cut into strips for the stress-strain studies.

Preparation of the γ-irradiation cross-linked elastomers: A quantity of 120 mg of dry sample was placed in the bottom of a cryotube to which 204 μL of distilled water were added. The samples were allowed to hydrate at 4° C. to form a viscoelastic mass. In each tube a Plexiglas pestle was then inserted which had a 1 mm×10 mm channel turned in it. As the pestle was inserted, the viscoelastic sample flowed into and filled the channel to form a continuous band with dimensions of 28 mm×10 mm×1 mm. The P(HP)P samples within the channel were held at 65° C. for 17 hours with slow rotation of the pestle. The samples were then placed in dry ice and taken to the γ-irradiation source. Irradiation cross-linking of the samples was carried out at the Auburn University Nuclear Science Center. The samples were placed at the center of a group of cobalt sources arranged in concentric circles. The configuration gave approximately 0.45 MRAD per hour gamma irradiation. The samples were exposed for 44.19 hours to give a total of 20 MRADs. The elastomeric bands are referred to as $X^{20}$-PPP for the cross-linked polypentapeptide, $X^{20}$-(PHP+PPP) for the cross-linked 1:2 mixture, respectively, of polyhexapeptide and polypentapeptide and $X^{20}$-P(HP)P for the cosequential polyhexapentapeptide with a random mixture of hexapeptide to pentapeptide (1:2) in the original polymerization.

Stress-strain studies: A strip of the polyhexapeptide sheet measuring 24 mm×4.64 mm×0.28 mm was clamped in the stress-strain apparatus with the distance between the grips being 10 mm. Elongation of the sample was done at a rate of 1.1 mm/min. The X-axis of the plotter recording the displacement of the moving grip was calibrated to 25.4 mm pen movement for a 0.1 mm grip displacement. The Statham UC-2 transducer with a UL4-2 load cell accessory used in our apparatus has a sensing element displacement of $2.15 \times 10^{-4}$ mm/gram of applied force. This correction was applied in calculating the elastic (Young's) modulus. The cross-section of each of the $\gamma$-irradiation cross-linked samples was measured prior to and after completion of each run. The elastic modulus of each sample was measured at 40° C. in water. The cross-linked cosequential polypeptide, $X^{20}$-P(HP)P, samples were then allowed to set for 12 hours at 65° C. and again the elastic modulus was measured at 40° C. The $X^{20}$-P(HP)P samples were subsequently swollen at 20° C. in water for five hours, heated at 80° C. in water for 17 hours and then the elastic moduli were again determined. During $\gamma$-irradiation cross-linking of some samples, vacuoles formed. When elastic moduli were determined no correction was made for the cross-sectional area of the vacuoles such that the elastic moduli are minimal values and can generally be considered to be about twice the value reported for the $X^{20}$-PPP and $X^{20}$-P(HP)P samples. The important element for the latter sample is the increase in elastic modulus on heat treatment at 65° C. and 80° C.

RESULTS

Aggregational Properties of Oligohexapeptides

When the hexapeptide (n=1) and the dodecapeptide (n=2) were examined, they exhibited little if any aggregation on raising the temperature to 80° C. When the octadecapeptide (n=3) was examined, however, it gave a temperature profile for turbidity with a midpoint just above 70° C., thereby demonstrating aggregation of polypeptide chains. On immediately lowering the temperature the aggregates redissolved, but if the temperature was raised to 80° C. and held there for a short period, the association in water did not reverse on standing overnight at 4° C. When the tetraeicosapeptide (n=4) was examined, the midpoint for the turbidity profile was shifted to a lower temperature, 57° C. This aggregation was found to be irreversible in water. Thus for the oligohexapeptides a repeating sequence of three to four hexapeptides is required before the polyhexapeptide-polyhexapeptide interaction is irreversible. To achieve irreversibility with heating at temperatures less than 80° C. an n of four is required.

The turbidity profiles for high molecular weight polyhexapeptide (n=100) were determined. The polyhexapeptide-polyhexapeptide interaction was irreversible in water, and dissolution in trifluoroethanol and lyophilization with increasing amounts of water is required to again attain solubility in water at low temperatures. The turbidity profiles for a series of concentrations of high molecular weight polypentapeptide (n=100) were also determined. Aggregation was immediately reversible on lowering the temperature. In an initial test as to whether hexapeptide sequences might function in an interlocking role when randomly interspersed in a polypeptide chain comprised of mostly pentapeptide, the random cosequential polyhexapentapeptide, P(HP)P, was prepared as outlined in the Experimental Section. The turbidity profiles for P(HP)P as a function of concentration were also determined. The aggregates, formed by heating this random copolymer of hexapeptide and pentapeptide with a ratio of 1:2, respectively, immediately redissolved on lowering the temperature below 25° C. If there are in the P(HP)P sufficiently long runs of uninterrupted repeating hexapeptides to effect some interlocking at elevated tempecatures, these associations are separated by the hydration (swelling) of pentamer sequences on lowering the temperature. Whether such associations might be present at 40° C. can be tested in the cross-linked samples by the stress-strain studies reported below.

When a lower molecular weight polyhexapeptide with n=40 is placed in one chamber of a tandem cell and polypentapeptide in the other, delayed turbitity was seen as the temperature was increased. The delayed turbidity change is believed to be due to aggregation of the lower molecular weight polyhexapeptide. On mixing the separately aggregated PHP and PPP, the PHP aggregation is not reversed on standing at 4° C. for more than 12 hours. If however the lower molecular weight PHP and the PPP are mixed at low temperature as solutions, on immediately lowering the temperature all aggregates redissolve. This indicates that there is significant PHP-PPP association on raising the temperature. When higher molecular weight PHP (n=100) and PPP (n=100) are combined as solutions at low temperature, a mixed aggregation is seen. This mixed aggregation does not redissolve on standing at 4° C. for several days. This demonstrates that there also can occur sufficient PHP-PHP interaction in the presence of PPP to achieve irreversibility i.e. interlocking.

Stress-Strain Studies

With 20 MRAD $\gamma$-irradiation of polypentapeptide carried out in the same manner as with the hexapeptide containing samples, the elastic modulus of the cross-linked polypentapeptide, $X^{20}$-PPP, was in the range of 2 to $3 \times 10^5$ dynes/cm$^2$ with the measurement taking place in water at 40° C. A stress-strain curve can be used to compare polypeptides modified to contain hexamer units. As a reference for the cellophane-like polyhexapeptide, a sheet of PHP was cast from a high concentration in trifluoroethanol. The elastic modulus of this strip was found to be $7 \times 10^9$ dynes/cm$^2$. A representative sample of cosequential polyhexapentapeptide, cross-linked by 20 MRAD $\gamma$-irradiation, i.e. $X^{20}$-P(HP)P, gave an initial value of $2.2 \times 10^5$ dynes/cm$^2$. On heating in water at 65° C. for 12 hours and re-examining at 40° C. in water, the elastic modulus had increased to $4.2 \times 10^5$ dynes/cm$^2$. The sample was then kept at 20° C. in water for 5 hours and then heated at 80° C. for 17 hours. The resulting elastic modulus at 40° C. in water had decreased to $3.3 \times 10^5$ dynes/cm$^2$. Averaged values for three samples were $1.9 \times 10^5$ dynes/cm$^2$, $4.2 \times 10^5$ dynes/cm$^2$ and $3.4 \times 10^5$ dynes/cm$^2$; these are for the initial values, the value after heat treatment at 65° C. and the value after heating at 80° C., respectively. The rationale for the choice of temperatures for the heat treatments derives from the turbidity profiles for the oligohexapeptides. A temperature of 65° C. resulted in irreversible association of oligohexapeptides with n=4. It would appear from the near doubling of elastic modulus on heating at 65° C. that some association of hexapeptide units did occur which functioned like additional crosslinks. Irreversible association of oligohexapeptides with n=3 did not occur until 80° C. but association of P(HP)P was completely reversed on going below 25° C. (see results of aggregation studies above). On this basis the $X^{20}$-P(HP)P, that had been heated at 65° C., was allowed to swell at 20° C. for 5 hours. In analogy to the reversible aggregation of P(HP)P, this is expected to reverse all hexapeptidehexapeptide interactions. The samples were then heated at 80° C. to see if additional putative (hexapeptide)$_n$-(hexapeptide)$_n$ associations might occur. This treatment caused a decrease in elastic modulus from what had been obtained after 65° C. treatment. While association of repeating hexapeptides with n=3 could possibly have been achieved, it is known that holding the temperature of PPP coacervate at 80° C. results in a very slow destructuring of the polypentapeptide. This and even the heat destructuring of the conformations of hexapeptide repeats within the cosequential polypeptide are possible explanations of the decrease in elastic modulus resulting from the 80° C. treatment.

Mixing polyhexapeptide with polypentapeptide in a 1:2 ratio produced polymers which were codissolved in a minimal amount of water (about 60% by weight) at 4° C. in the cryotube. The pestle was then inserted causing the viscoelastic solution to flow into the channel turned in the pestle. The pestle was rotated with the sample in an ice bath for several hours and the sample was then placed in dry ice until γ-irradiation at 20 MRAD. The product can be referred to as $X^{20}$-(PHP+PPP). The elastic modulus at between 50 to 60% extension was $2.6 \times 10^6$ dynes/cm$^2$. This value is essentially identical to that of natural fibrous elastin which similarly exhibits a lower initial slope. There is a marked reproducible hysteresis which is a result of the slow rate of retraction of the sample. The rate of change in length was approximately 1 mm/min.

In addition to the particular sequences noted above throughout the present specification, other sequences of amino acids may be incorporated in the elastomeric material of the present invention without limitation provided that the material so made retains elasticity and exhibits an inverse temperature transition and the properties associated therewith.

In particular, and for example, while the hexameric sequence described above (APGVGV), used to enhance the mechanical properties of a bioelastomer containing the same, is most often used, other hexameric sequences may also be used. In the sequence (APGVGV), instead of A, Val, Ile, Phe and Leu may be used. However, it is preferred that P be proline. Instead of P, Val, Ile, Phe, Leu or even Ala may be used. Instead of the first G, Ala may be used. Instead of the first V, Phe, Leu, Ile or Ala may be used. Instead of the second V, Phe, Leu, Ile, Val or Ala may be used.

Notably, occasional substitutions with the full range of known and available amino acids may be used with the proviso that the biocompatibility, biodegradability and elastomeric properties be maintained as has been disclosed in pending applications Ser. No. 062,557 and the continuation-in-part thereof.

Furthermore, in synthesizing the polypeptides of the present invention, since all of the amino acids present in the polypeptides of the invention have corresponding DNA codons, the polypeptides can be produced by genetic engineering using synthetic genes containing codons that correspond to the desired amino acid sequence.

II. The Use of the Present Elastomeric Materials for the Isolation of Wound Repair Sites in the Prevention of Adhesion Between a Damaged or Repaired Site and a Second Site The elastomeric materials of the present invention may be formed as strips and used as such, or the present elastomeric materials may be applied to the areas of wound repair sites such as incision sites or burn sites as powders, gels or foams.

If the elastomeric materials are applied to an incision, their application may appear as illustrated in FIG. 1. In particular, the elastomeric strip is applied to the surface of the incision and stitched thereto and the next layer would then be closed.

The present elastomeric materials may be applied, however, as powders, gels or foams, as for example in body cavities such as the abdomen and thorax. As a foam, the present elastomeric materials may be formulated similar to those disclosed in U.S. Pat. Nos. 3,969,498 and 4,495,168 which are both specifically incorporated herein the entirety.

Also, the present elastomeric materials may be applied as a gel. As such, they may be formulated similar to the gels disclosed in U.S. Pat. Nos. 4,291,025 and 4,393,048 which are both specifically incorporated herein in the entirety.

Additionally, the present elastomeric materials may also be applied as a powder to an incision site or wound repair area in a manner similar to that disclosed in U.S. Pat. No. 4,287,177, which is incorporated herein in the entirety.

In general, and regardless of whether the elastomeric materials of the present invention are applied as strips, ribbons or sheets or even as powders, gels, or foams, the rate at which the materials biodegrade will be determined, in part, by the thickness of the material applied. That is, applications of lesser amounts of powders, gels or foams and thinner strips, ribbons or sheets will result in a protective adhesion-preventing layer which will biodegrade at a relatively quicker rate. The converse will be true for thicker layers.

Additionally, it is also possible to slow the rate of biodegradation by incorporating D-amino acids in the peptide sequences or by incorporating L- or D-amino acids containing sterically large side-chains which would tend to inhibit enzymatic hydrolysis of the peptide bonds.

The elastomeric materials of the present invention may be applied with the ordinary skill of one performing surgery. In applying the present materials, an effective quantity of elastomeric material is applied in any desired form to the site undergoing repair. If the material is applied as a strip or ribbon or sheet, it may be conveniently sutured over an incision site or a burn area or any skin injury. If the material is added as a powder, which expands upon hydration, or a foam or gel, the material may either be sutured over the incision site or applied and left unsutured. Thereafter, the incision of the next layer is then sutured. As already noted, this places the elastomeric material as an elastic barrier separating the repair sites such that connective tissue will not form between the incisions of each layer or between repairing sites within a body cavity.

Generally, regardless of whether the elastomeric materials are applied as a gel, foam or powder or strip, as an approximation, as little as 1 mg or as much as 100 grams of material may be required within a body cavity or on the surface of an incision site or burn area or other skin injury or abrasion. If the elastomeric materials are applied as a sheet, ribbon or strip, or even as gels, foams or powders, a thickness of from about 0.001 inches to about 0.1 inches will generally be used. However, the thickness may be more or less as is needed.

Further, the present materials are preferably used in the cross-linked state as, thereby, they will have greater durability and ease of handling. The strips and ribbons of the present invention are used in a cross-linked state, whereas the foams, gels and powders are used in an uncrosslinked states.

The elastomeric materials of the present invention may be advantageously used in the protection of burn areas, incision sites, skin abrasions or other skin injuries in humans. However, the present elastomeric materials may also be so used with other mammals such as dog, cats, horses, cows or other farm and domestic animals in veterinary medicine.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for substantially preventing wound adhesion which comprises forming a protective layer between a mammalian wound repair site and a second tissue site wherein said protective layer comprises an elastomeric material capable of reversibly contracting and relaxing by inverse temperature transition wherein a change in chemical potential of a molecular species will effect a change in said inverse temperature transition, and wherein said elastomeric material comprises a bioelastomer containing repeating units selected from the group consisting of elastomeric tetrapeptide and pentapeptide repeating units wherein said repeating units comprise amino acid residues selected from the group consisting by hydrophobic amino acid and glycine residues, and wherein said repeating units exist in a conformation having a $\beta$-turn.

2. A method for substantially preventing wound adhesion which comprises forming a protective layer between a mammalian wound repair site and a second tissue site where said protective layer comprises an elastomeric material comprising a bioelastomer containing repeating units selected from the group consisting of elastomeric tetrapeptide and pentapeptide repeating unit wherein said repeating units comprise amino acid residues selected form the group consisting of hydrophobic amino acid and glycine residues, and wherein said repeating units exist in a conformation having a $\beta$-turn and said repeating units comprise a polypentapeptide unit of the formula:

$$-X^1-(IPGVG)_n-Y^1-$$

where
I is a peptide-forming residue of L-isoleucine;
P is a peptide-forming residue of L-proline;
G is a peptide-forming residue of glycine;
V is a peptide-forming residue of L-valine; and
wherein $X^1$ is PGVG, GVG, VG, G or a covalent bond; $Y^1$ is IPGV, IPG, IP, I or a covalent bond; and n is an integer from 1 to 5,000, or n is 0, with the proviso that $X^1$ and $Y^1$ together constitute at least one of said pentameric unit.

3. A method for substantially preventing wound adhesion which comprises forming a protective layer between a mammalian wound repair site and a second tissue site wherein said protective layer comprises an elastomeric material comprising a bioelastomer containing repeating units selected from the group consisting of elastomeric tetrapeptide and pentapeptide repeating units wherein said repeating units comprises amino acid residues selected from the group consisting of hydrophobic amino acid and glycine residues, and wherein said repeating units exist in a conformation having a $\beta$-turn and said repeating units comprise A) a polypentapeptide unit of the formula:

$$-X^1-(IPGVG)_n-Y^1-$$

and

B) a polypentapeptide unit of the formula:

$$-X^2-(VPGVG)_n-Y^2-$$

wherein for the above formula,
I is a peptide-forming residue of L-isoleucine;
P is a peptide-forming residue of L-proline;
G is a peptide-forming residue of glycine;
V is a peptide-forming residue of L-valine; and
wherein $X^1$ and $X^2$ are each PGVG, GVG, VG, G or a covalent bond; $Y^1$ is IPGV, IPG, IP, I or a covalent bond; $Y^2$ is VPGV, VPG, VG, G or a covalent bond; and n in both formulas is an integer from 1 to 200, or n is 0, with the proviso that $X^1$ and $Y^1$ or $X^2$ and $Y^2$ together constitute at least one of said pentameric unit.

4. A method for substantially preventing wound adhesion which comprises forming a protective layer between a mammalian wound repair site and a second tissue site wherein said protective layer comprises an elastomeric material comprising a bioelastomer containing repeating units selected from the group consisting of elastomeric tetrapeptide and pentapeptide repeating units wherein said repeating units comprise amino acid residues selected from the group consisting of hydrophobic amino acid and glycine residues, and wherein said repeating units exist in a conformation having a $\beta$-tun and said repeating units comprise a tetrapeptide of the formula:

$$-X^3-(VPGG)_n-Y^3-$$

wherein
$X^3$ is PGG, GG, G or a covalent bond;
$Y^3$ is VPG, VP, V or a covalent bond;
and V is a peptide-producing residue of L-valine; P is a peptide-producing residue of L-proline; and G is a peptide-producing residue of glycine; and n is an integer from 1 to 200, or n is 0, with the proviso that $X^3$ and $Y^3$ together constitute at least one of said tetrameric unit.

5. A method for substantially preventing wound adhesion which comprises forming a protective layer between a mammalian wound repair site and a second tissue site wherein said protective layer comprises and elastomeric material comprising a bioelastomer containing repeating units selected from the group consisting of elastomeric tetrapeptide and pentapeptide repeating units wherein said repeating units comprise amino acid residues selected from the group consisting of hydrophobic amino acid and glycine residues, and wherein said repeating units exist in a conformation having a β-turn and said repeating units comprise a tetrapeptide of the formula:

—X⁴—(IPGG)ₙ—Y⁴— wherein
X⁴ is PGG, GG, G or a covalent bond; Y⁴ is IPG, IP, I or a covalent bond; and
I is a peptide-producing residue of L-isoleucine;
P is a peptide-producing residue of L-proline; and
G is a peptide-producing residue of glycine; and n is an integer from 1 to 200, or n is 0, with the proviso that X⁴ and Y⁴ together constitute at least one of said tetrameric unit.

6. A method for substantially preventing wound adhesion which comprises forming a protective layer between a mammalian wound repair site and a second tissue site wherein said protective layer comprises an elastomeric material comprising a bioelastomer containing repeating units selected from the group consisting of elastomeric tetrapeptide and pentapeptide repeating units wherein said repeating unit comprise amino acid residues selected from the group consisting of hydrophobic amino acid and glycine residues, and wherein said repeating units exist in a conformation having a β-turn and said repeating units comprise a pentapeptide repeating unit of the formula:

(R₁PR₂R₃G)ₙ wherein R₁ is a peptide-producing residue selected from the group consisting of Phe, Leu, Ile, and Val; R² is such a residue selected from the group consisting of Ala and Gly; R₃ is such a residue selected from the group consisting of Phe, Leu, Ile, and Val; P is a L-proline-producing residue, and G is a glycine-producing residue, and n is an integer from 1 to about 5,000.

7. A method for substantially preventing wound adhesion which comprises forming a protective layer between a mammalian wound repair set and a second tissue site wherein said protective layer comprises an elastomeric material comprising a bioelastomer containing repeating units selected from the group consisting of elastomeric tetrapeptide and pentapeptide repeating units wherein said repeating units comprise amino acid residues selected from the group consisting of hydrophobic amino acid and glycine residues, and wherein said repeating units exits in conformation having a β-turn and said repeating units comprise a tetrapeptide repeating unit of the formula:

(R₁PGG)ₙ wherein R¹ is a peptide-producing residue selected from the group consisting of Phe, Leu, Ile, and Val; P is a L-proline-producing residue, and G is a glycine-producing residue, and n is an integer from 1 to about 5,000.

8. A method for substantially preventing wound adhesion which comprises forming a protective layer between a mammalian wound repair site and a second tissue site wherein said protective layer comprises an elastomeric material comprising repeating units comprise a polypentapeptide unit of the formula:

—X¹—(VPGVG)—Y¹— wherein
V is a peptide-forming residue of L-valine;
P is a peptide-forming residue of L-proline;
G is a peptide-forming residue of glycine; and
wherein X¹ is PGVG, GVG, VG or G or a covalent bond; Y¹ is VPGV, VPG, VP or V or a covalent bond; and n is an integer from 1 to about 5,000, or n is 0, with the proviso that X¹ and Y¹ together constitute at least one of said pentameric unit.

9. The method of any one of claims 1-8, wherein said elastomeric material is in the form of a strip, ribbon or sheet.

10. The method of any one of claims 1-8, wherein said elastomeric material is in the form of a powder, gel or foam.

11. The method of any one of claim s 1-8, wherein said elastomeric material is substantially cross-linked.

12. The method of any one of claims 1-8, wherein said elastomeric material is substantially uncrosslinked.

13. The method of any one of claim s 1-8, wherein said bioelastomer additionally comprise hexapeptide repeating units of the formula:

—X(APGVGV)ₙ—Y— wherein
A is a peptide-forming residue of L-alanine;
P is a peptide-forming residue of L-proline;
G is a peptide-forming residue of glycine;
V is a peptide-forming residue of L-valine;
and X is PGVGV, GVGV, VGV, GV, V or a covalent bond; Y is APGVG, APGV, APG, AP, A or a covalent bond; and n is an integer of from 2 to about 5,000, wherein this hexameric segment contains at least 18 amino acid residues.

14. The method of any one of claims 1-8, wherein said method steps comprise:
preparing said elastomeric material comprising a bioelastomer containing repeating units selected from the group consisting of elastomeric tetrapeptide and pentapeptide repeating units and combinations thereof, and
applying an effective amount of said elastomeric material to said mammalian wound repair site, wherein said elastomeric material forms a barrier to isolate said mammalian wound repair site such that connective tissue will not form between said mammalian wound repair site and said second tissue site.

15. The method of claim 14, wherein said bioelastomers contain repeating sequences that occur naturally within the elastic fiber of biological connective tissue.

16. The method of any one of claims 1-8, where said mammalian wound repair site is an incision or a burn.

17. The method of any one of claims 1-8, wherein said elastomeric material is biodegradable.

18. The method of any one of claims 1-8, wherein said elastomeric material is readily steilizable.

19. The method of any one of claims 1-8, wherein said elastomeric material elicits insignificant immunogenic or antigenic responses.

* * * * *